(12) United States Patent
Smith et al.

(10) Patent No.: US 11,617,875 B2
(45) Date of Patent: Apr. 4, 2023

(54) POSITIVE DISPLACEMENT SHUTTLE PUMP HEART AND VAD

(71) Applicant: SummaCor, Inc., San Diego, CA (US)

(72) Inventors: Steve C. Smith, Trabuco Canyon, CA (US); David J. Cline, Newport Beach, CA (US)

(73) Assignee: SummaCor, Inc., San Diego, CA (US)

( * ) Notice: Subject to any disclaimer, the term of this patent is extended or adjusted under 35 U.S.C. 154(b) by 390 days.

(21) Appl. No.: 16/867,361

(22) Filed: May 5, 2020

(65) Prior Publication Data

US 2020/0282119 A1    Sep. 10, 2020

Related U.S. Application Data

(63) Continuation of application No. PCT/US2020/021591, filed on Mar. 6, 2020.
(Continued)

(51) Int. Cl.
*A61M 60/419* (2021.01)
*A61L 27/02* (2006.01)
(Continued)

(52) U.S. Cl.
CPC .......... *A61M 60/419* (2021.01); *A61L 27/025* (2013.01); *A61L 27/10* (2013.01); *A61M 60/178* (2021.01); *A61M 60/258* (2021.01); *A61M 60/462* (2021.01); *A61M 60/554* (2021.01); *A61M 60/857* (2021.01); *A61M 60/873* (2021.01); *A61M 60/876* (2021.01);
(Continued)

(58) Field of Classification Search
CPC .. A61M 60/122; A61M 60/126; A61M 60/13; A61M 60/104; A61M 60/00; A61M 60/10; A61M 60/165; A61M 60/462; A61M 60/459
See application file for complete search history.

(56) References Cited

U.S. PATENT DOCUMENTS

| 1,959,106 | A | * | 5/1934 | Messing | ................. F04D 17/14 34/191 |
| 3,464,359 | A | | 9/1969 | King et al. | |

(Continued)

FOREIGN PATENT DOCUMENTS

| CN | 108514661 A | * | 9/2018 | ............ A61M 1/101 |
| JP | S5279303 A | | 7/1977 | |

(Continued)

OTHER PUBLICATIONS

International Search Report and Written Opinion dated Jul. 23, 2020, for International Application No. PCT/US2020/021591, 15 pages.
(Continued)

*Primary Examiner* — Scott J Medway
(74) *Attorney, Agent, or Firm* — Cooley LLP

(57) ABSTRACT

Described herein are devices and methods for pumping blood in a patient in need of circulatory assistance or a replacement heart. Instead of providing a temporary solution for these patients, the devices may be permanently implanted. The devices linearly reciprocate a shuttle within a housing to move blood into and out of the housing, and rotate the shuttle to selectively direct the movement of blood into and out of a plurality of ports in the housing.

28 Claims, 25 Drawing Sheets

Related U.S. Application Data

(60) Provisional application No. 62/816,056, filed on Mar. 8, 2019.

(51) Int. Cl.
*A61L 27/10* (2006.01)
*A61M 60/857* (2021.01)
*A61M 60/178* (2021.01)
*A61M 60/462* (2021.01)
*A61M 60/554* (2021.01)
*A61M 60/892* (2021.01)
*A61M 60/876* (2021.01)
*A61M 60/873* (2021.01)
*A61M 60/258* (2021.01)

(52) U.S. Cl.
CPC ........ *A61M 60/892* (2021.01); *A61L 2430/20* (2013.01); *A61M 2205/0211* (2013.01); *A61M 2205/0238* (2013.01); *A61M 2205/3331* (2013.01); *A61M 2205/3592* (2013.01); *A61M 2205/8206* (2013.01)

(56) References Cited

U.S. PATENT DOCUMENTS

| | | | |
|---|---|---|---|
| 3,791,769 A * | 2/1974 | Kovacs | A61M 60/117 417/413.1 |
| 4,192,348 A | 3/1980 | Hansen | |
| 4,210,409 A | 7/1980 | Child | |
| 4,375,941 A | 3/1983 | Child | |
| 4,850,980 A | 7/1989 | Lentz et al. | |
| 5,108,426 A | 4/1992 | Biro et al. | |
| 5,158,441 A * | 10/1992 | Aid | F04B 7/06 417/500 |
| 5,300,111 A * | 4/1994 | Panton | A61M 60/196 623/3.19 |
| 5,312,233 A | 5/1994 | Tanny et al. | |
| 5,368,439 A * | 11/1994 | Piazza | F04D 29/622 415/131 |
| 5,443,503 A * | 8/1995 | Yamane | A61M 60/422 600/16 |
| 5,456,715 A | 10/1995 | Liotta | |
| 5,674,281 A * | 10/1997 | Snyder | A61M 60/446 623/3.28 |
| 5,676,651 A * | 10/1997 | Larson, Jr. | A61M 60/554 604/33 |
| 5,695,471 A * | 12/1997 | Wampler | A61M 60/538 417/423.1 |
| 6,158,984 A * | 12/2000 | Cao | A61M 60/232 417/423.1 |
| 6,193,473 B1 * | 2/2001 | Mruk | F04D 25/06 310/179 |
| 6,201,329 B1 * | 3/2001 | Chen | F16C 32/0444 417/423.1 |
| 6,290,640 B1 | 9/2001 | Goldowsky | |
| 6,375,086 B1 * | 4/2002 | Babin | F25B 41/35 236/92 B |
| 6,395,027 B1 | 5/2002 | Snyder | |
| 6,422,838 B1 * | 7/2002 | Sloteman | F04D 13/0666 417/247 |
| 6,436,027 B1 * | 8/2002 | Goldowsky | A61M 60/824 600/16 |
| 6,511,298 B2 * | 1/2003 | Takura | F04D 13/0606 417/423.15 |
| 6,511,413 B2 | 1/2003 | Landesberg | |
| 6,619,935 B1 * | 9/2003 | Kluth | F04D 29/042 417/423.1 |
| 6,723,039 B2 | 4/2004 | French et al. | |
| 6,969,345 B2 | 11/2005 | Jassawalla et al. | |
| 7,811,221 B2 | 10/2010 | Gross | |
| 7,850,593 B2 | 12/2010 | Vincent et al. | |
| 7,988,655 B2 | 8/2011 | Rakhorst et al. | |
| 8,157,720 B2 | 4/2012 | Marseille et al. | |
| 8,398,934 B2 | 3/2013 | Bensley | |
| 8,449,443 B2 | 5/2013 | Rodefeld et al. | |
| 8,574,291 B2 | 11/2013 | Finocchiaro et al. | |
| 8,597,350 B2 | 12/2013 | Rudser et al. | |
| 8,608,798 B2 | 12/2013 | Wampler | |
| 9,002,469 B2 | 4/2015 | D'Ambrosio | |
| 9,314,559 B2 * | 4/2016 | Smith | A61M 60/873 |
| 9,364,596 B2 | 6/2016 | Vadala, Jr. et al. | |
| 9,433,714 B2 | 9/2016 | Voskoboynikov et al. | |
| 9,433,716 B2 | 9/2016 | Vadala, Jr. et al. | |
| 9,446,180 B2 | 9/2016 | Vadala, Jr. et al. | |
| 9,555,173 B2 | 1/2017 | Spanier | |
| 10,188,779 B1 | 1/2019 | Polverelli et al. | |
| 10,398,821 B2 | 9/2019 | Botterbusch et al. | |
| 10,568,999 B2 | 2/2020 | Gross | |
| 2006/0245959 A1 * | 11/2006 | LaRose | A61M 60/824 417/423.5 |
| 2007/0237658 A1 | 10/2007 | Burns et al. | |
| 2007/0253842 A1 * | 11/2007 | Horvath | A61M 60/822 417/350 |
| 2008/0187449 A1 | 8/2008 | Breidenbach | |
| 2008/0294040 A1 | 11/2008 | Mohiuddin et al. | |
| 2009/0149950 A1 * | 6/2009 | Wampler | A61M 60/232 623/3.13 |
| 2010/0109463 A1 * | 5/2010 | Jiang | F16C 32/0417 310/90.5 |
| 2011/0201870 A1 * | 8/2011 | Forsell | A61M 60/873 600/16 |
| 2012/0053557 A1 | 3/2012 | Abal | |
| 2012/0178986 A1 * | 7/2012 | Campbell | A61M 60/13 600/16 |
| 2012/0245678 A1 | 9/2012 | Solem | |
| 2013/0138205 A1 | 5/2013 | Kushwaha et al. | |
| 2014/0155998 A1 | 6/2014 | Wampler | |
| 2014/0179993 A1 | 6/2014 | Alexander et al. | |
| 2016/0045652 A1 | 2/2016 | Cornen | |
| 2018/0169316 A1 | 6/2018 | Lo et al. | |
| 2018/0207337 A1 | 7/2018 | Spence et al. | |
| 2019/0167877 A1 | 6/2019 | Gross | |
| 2019/0216995 A1 | 7/2019 | Kapur et al. | |
| 2019/0255236 A1 | 8/2019 | Gross | |
| 2019/0255237 A1 | 8/2019 | Cinbis | |
| 2019/0275225 A1 | 9/2019 | Brown | |
| 2019/0288565 A1 | 9/2019 | Martinez et al. | |
| 2019/0290819 A1 | 9/2019 | Hansen | |
| 2019/0323492 A1 | 10/2019 | Tracey et al. | |
| 2019/0358383 A1 | 11/2019 | Reyes et al. | |
| 2019/0365993 A1 | 12/2019 | Staub et al. | |
| 2019/0381227 A1 | 12/2019 | Botterbusch et al. | |
| 2020/0000999 A1 | 1/2020 | Batchinsky et al. | |
| 2021/0113826 A1 | 4/2021 | Smith et al. | |
| 2022/0072295 A1 | 3/2022 | Smith et al. | |
| 2022/0265989 A1 | 8/2022 | Smith et al. | |

FOREIGN PATENT DOCUMENTS

| | | | | |
|---|---|---|---|---|
| WO | WO-2011069109 A2 * | 6/2011 | .......... | A61M 1/1036 |
| WO | WO-2014140282 A1 * | 9/2014 | ............. | A61B 5/076 |

OTHER PUBLICATIONS

International Search Report and Written Opinion dated Feb. 8, 2021, for International Application No. PCT/US2020/056142, 11 pages.
Garbade et al., "Current Trends in Implantable Left Ventricular Assist Devices," Cardiology Research and Practice, vol. 2011, Article ID 290561, Mar. 1, 2011, 9 pages.
Patel, "Design and Development of a Pulsatile Axial Flow Blood Pump as a Left Ventricular Assist Device," Brunel Institute for Bioengineering, Brunel University, Dec. 2011, 209 pages.
Pulsatile Blood Pumps, product information page, 3 pages, https://www.harvardapparatus.com/catalog/product/view/id/8294/s/pulsatile-blood-pumps/category/515/.
International Search Report and Written Opinion for Application No. PCT/US21/49166, dated Dec. 20, 2021, 13 pages.
International Preliminary Report on Patentability for Application No. PCT/US2020/021591, dated Sep. 23, 2020, 13 pages.

(56) References Cited

OTHER PUBLICATIONS

International Search Report and Written Opinion for International Application No. PCT/US2022/017098 dated Jun. 29, 2022, 18 pages.
International Search Report and Written Opinion dated Dec. 20, 2021, for International Application No. PCT/US2021/049166, 13 pages.
Invitation to Pay for International Application No. PCT/US2022/017098 dated Apr. 19, 2022, 2 pages.
Extended European Search Report for European Application No. 20770326.5 dated Nov. 30, 2022, 5 pages.

* cited by examiner

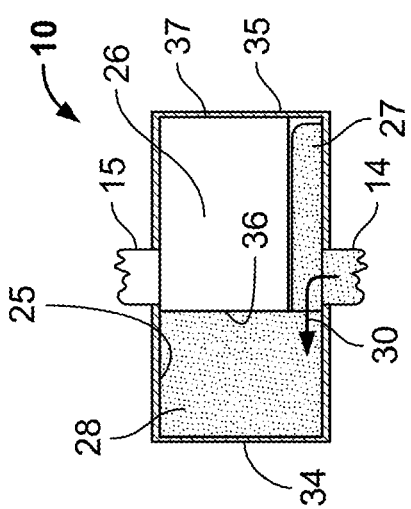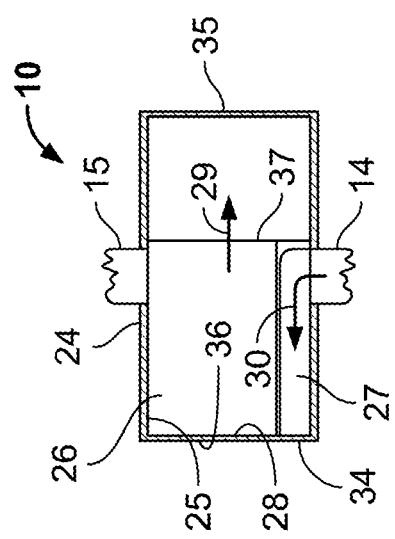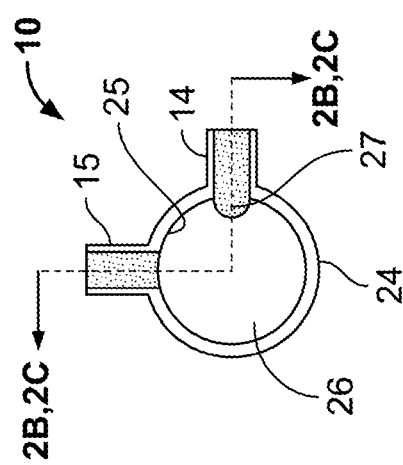
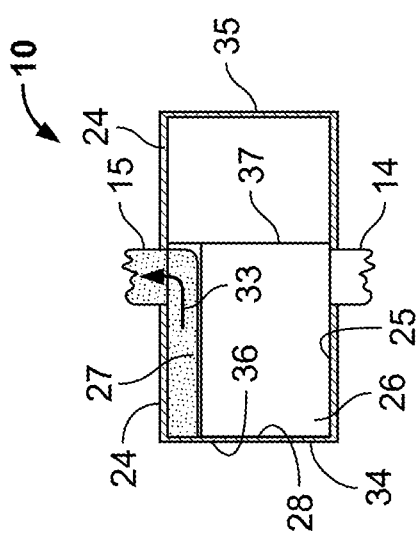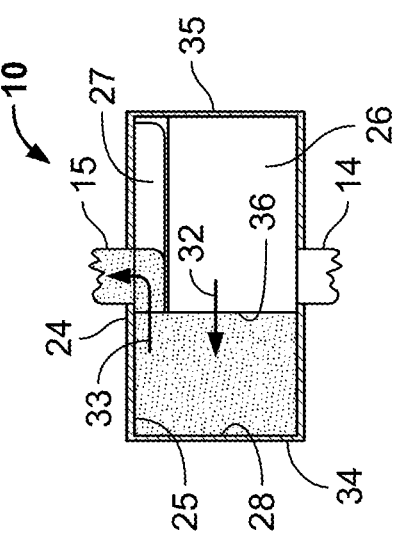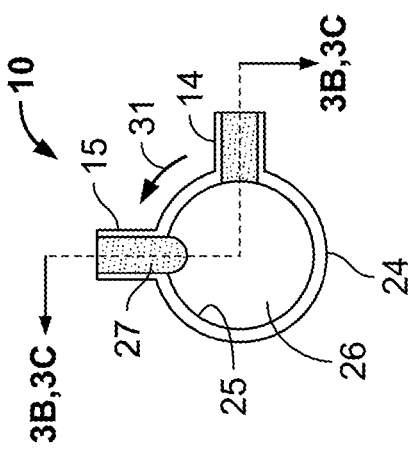

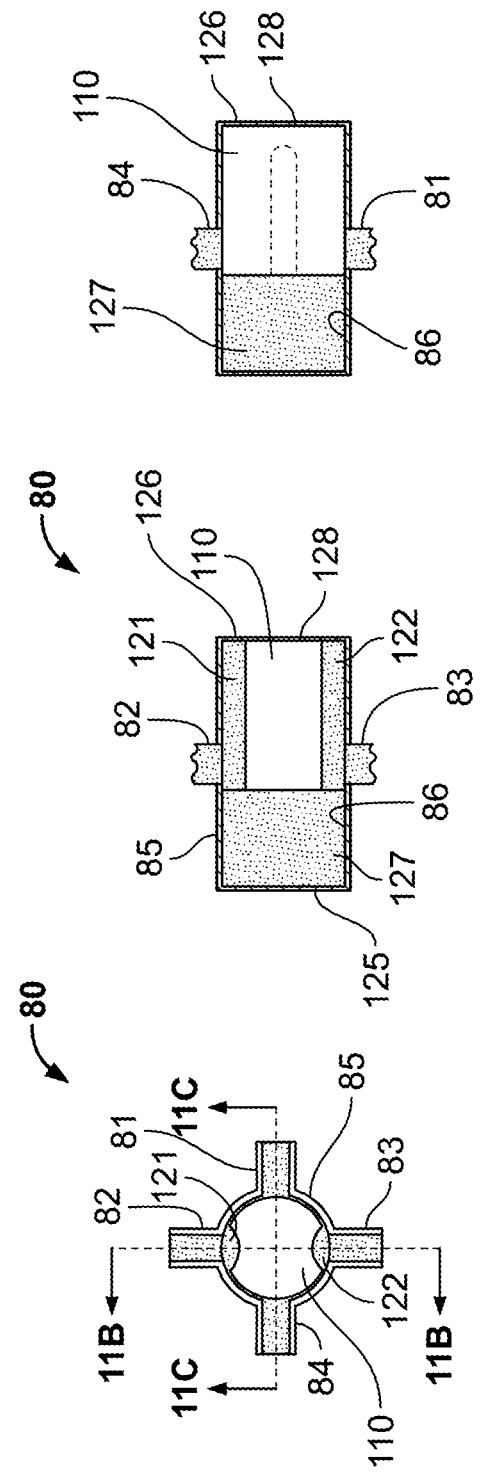

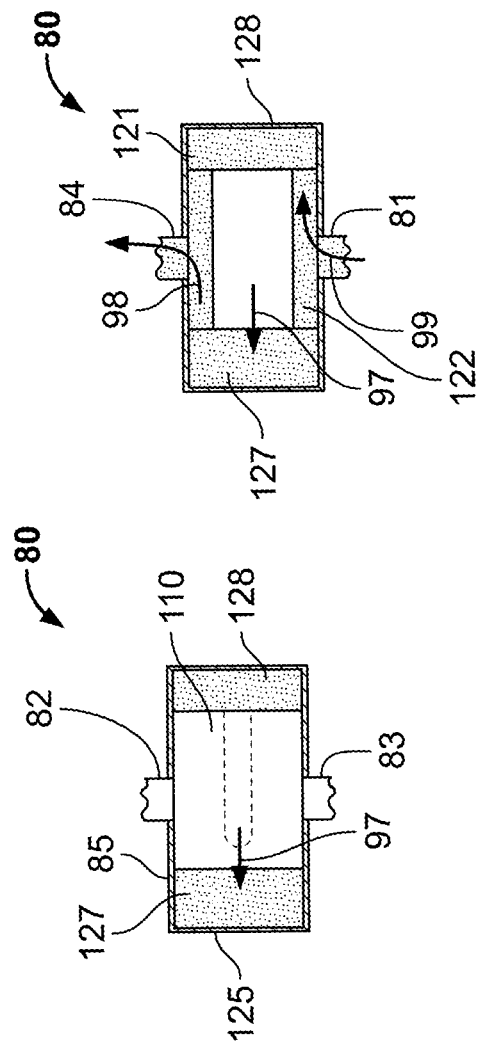

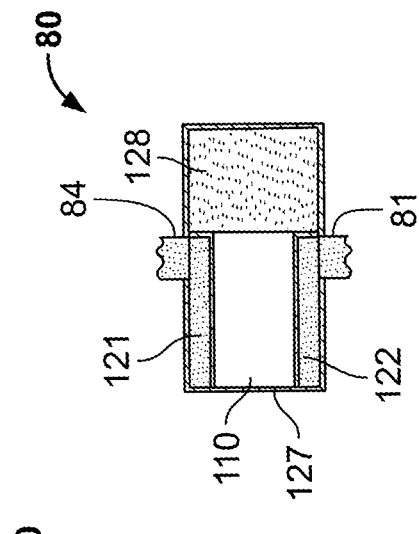
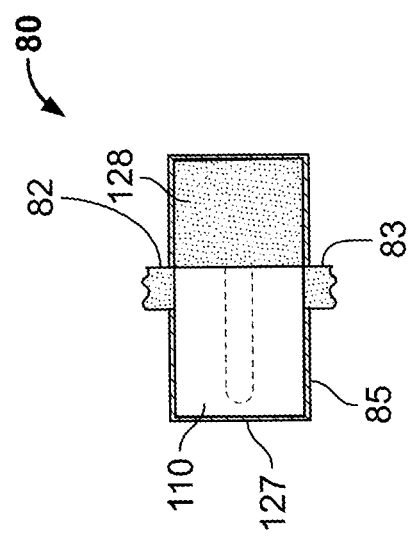
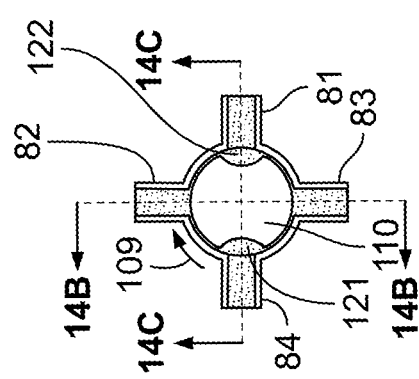

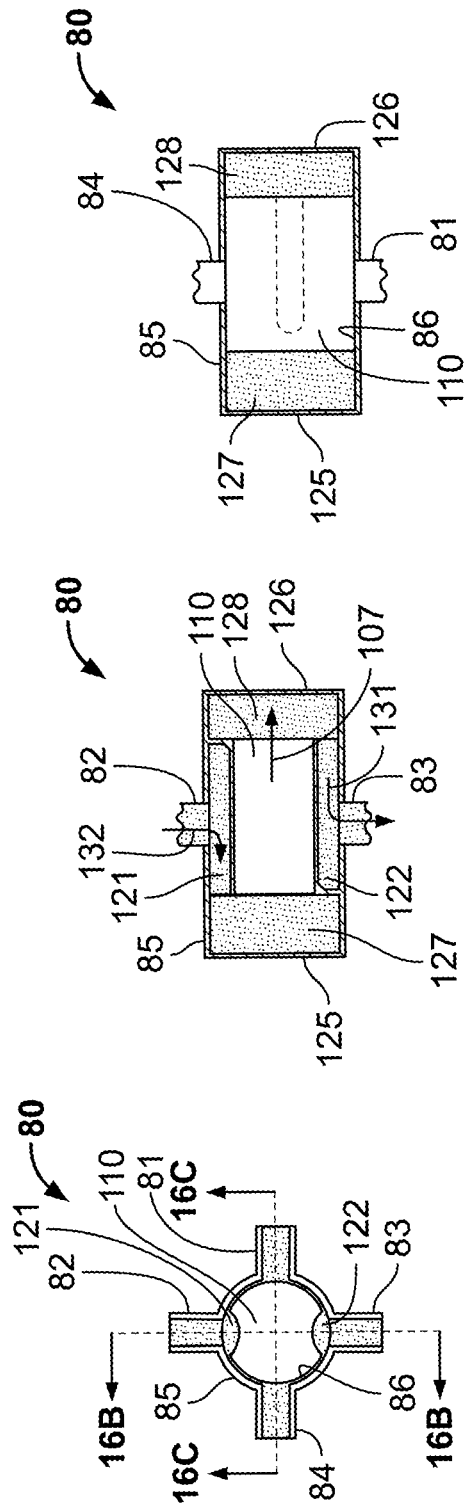

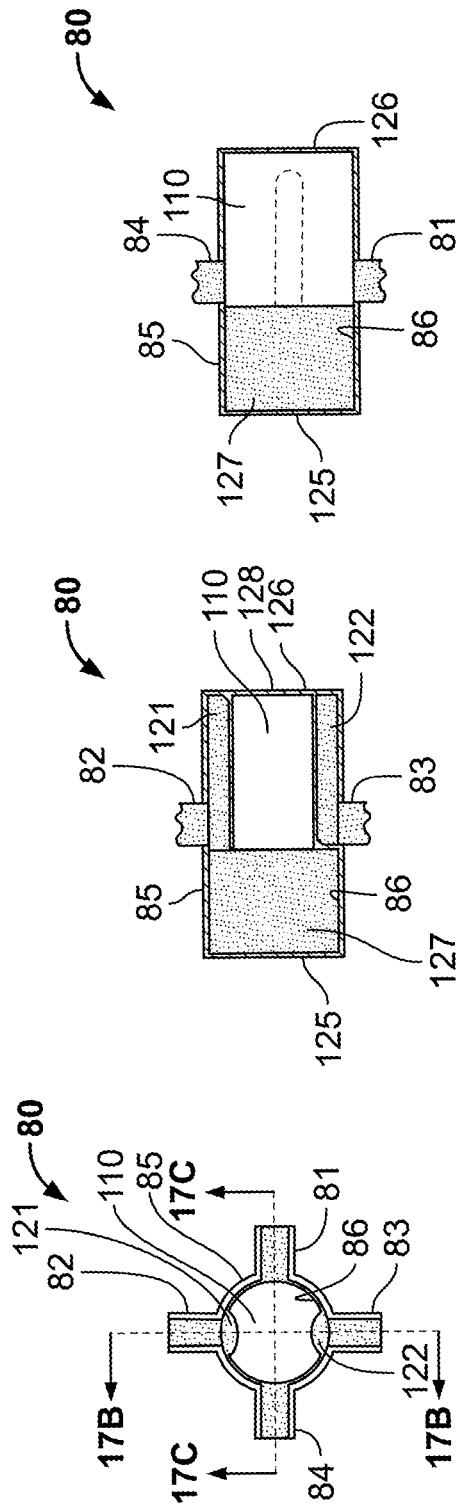

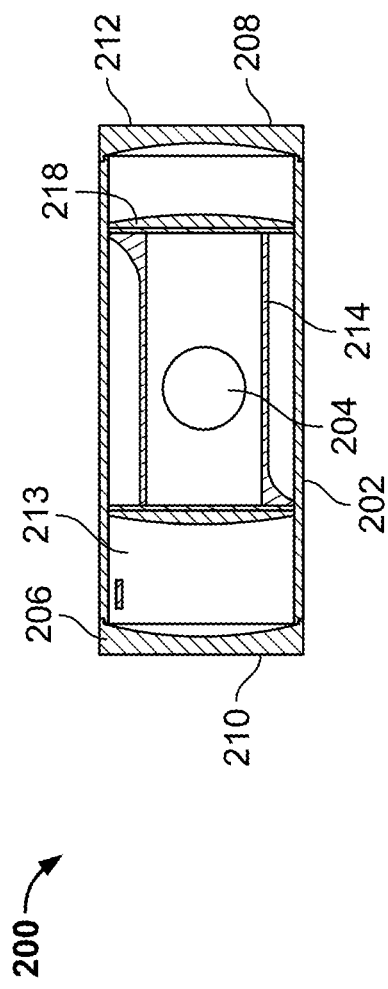
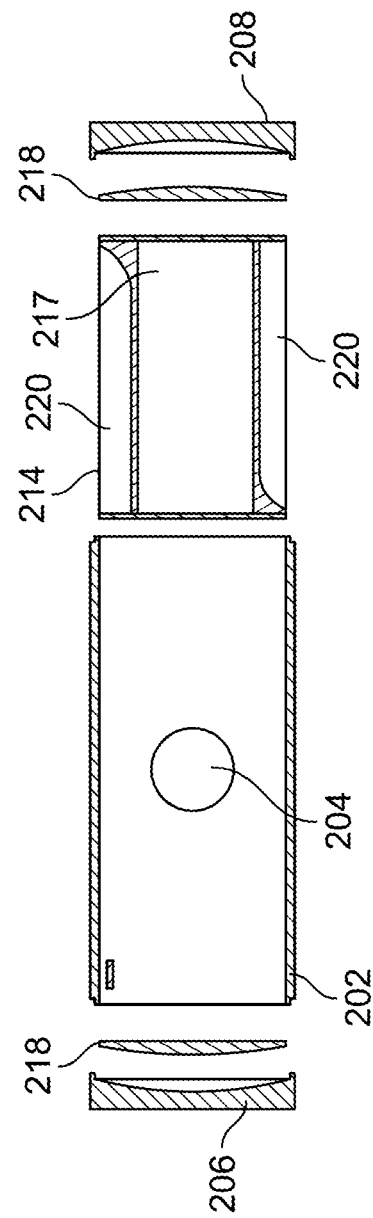

POSITIVE DISPLACEMENT SHUTTLE PUMP HEART AND VAD

CROSS-REFERENCE TO RELATED APPLICATIONS

This application is a continuation of International Application No. PCT/US2020/021591, filed on Mar. 6, 2020, which claims priority to U.S. Provisional Application Ser. No. 62/816,056, filed on Mar. 8, 2019, the disclosure of each of which is hereby incorporated by reference in its entirety.

FIELD OF THE INVENTION

This application generally relates to pump devices and methods for sustaining and continuing life for patients having poorly performing, failing or failed hearts, and particularly to artificial devices, known generally in the art as "artificial hearts" and "ventricular assist devices" (VADs).

BACKGROUND OF THE INVENTION

For many years, practitioners in the medical treatment and medical device arts have endeavored to provide artificial heart devices constructed to supplement, or fully replace, a poorly performing heart, a failed heart or failing heart within a patient recipient. The most basic long term need is the creation of a replacement pumping device which is capable of being implanted within a patient to fully replace the natural heart and perform the basic blood pumping and circulation functions of the natural heart. An additional need exists for a supplemental device intended to aid a poorly performing or failing heart, often on a more short term basis, but not usually intended to completely replace the natural heart. Such "supplemental" devices are referred to as "Ventricular Assist Devices" (VADs) such as "Left Ventricular Assist Devices" (LVADs) and "Right Ventricular Assist Devices" (RVADs).

Early attempts to provide a sustainable heart replacement were severely limited by the available technologies and the state of the art at that time. Available devices proved to be generally too large and unwieldy and, for the most part, impractical. With the continuing advances in the related technologies and creative arts, heart replacement devices became smaller, more reliable and, in some instances, at least partially implantable within the recipient. Such "implantable" devices have generally remained hybrid devices in that the actual pump may be implanted within the recipient while additional support apparatus remains external to the patient and remains connected to the implanted device by a plurality of connecting wires and hoses. Despite advances, a fully implantable practical artificial heart has remained elusive and largely unobtainable.

The demands to be made upon an artificial heart or ventricular assist device remain daunting. A successful artificial heart or implantable ventricular assist device must, above all, be long lasting and reliable. The dire consequences to the device recipient brought about by device failure make this requirement all too apparent. Given that currently available devices pump blood using spinning components, which must rotate at high speeds to achieve adequate blood flow and pressure, they provide a temporary solution for heart failure, serving as a bridge to heart transplant.

In addition, the device must be small enough to be implantable within the recipient's chest and efficient enough to maintain adequate blood circulation to sustain normal life functions. The device must avoid undue stress upon the recipient's circulatory and pulmonary systems. The device must also be capable of adjusting to and compensating for different recipient activity levels and stresses. Additional requirements such as avoidance of turbulence within the blood flow as well as avoidance of blood cell damage by the pumping apparatus and the prevention of blood clot forming stagnation regions make further demands upon artificial heart and ventricular assist devices.

Thus, while practitioners in the medical treatment and medical device arts have created a virtually endless variety of proposed artificial heart and ventricular assist devices, there remains nonetheless a continuing unresolved need in the art for improved, implantable, reliable and effective artificial hearts and ventricular assist devices which meet the stringent, unforgiving and vital requirements and challenges posed by a truly fully functioning completely implantable artificial heart or ventricular assist device.

Accordingly, it would be useful to have improved ventricular assist devices and artificial heart devices.

SUMMARY

Described herein are devices and methods for pumping blood in a patient in need of circulatory assistance or a replacement heart. Instead of providing a temporary solution for these patients (recipients), the devices may be permanently implanted. Device features that may permit permanent implantation include, but are not limited to, the lack of an impeller that must rotate at high speed to efficiently pump blood, a shuttle that primarily generates blood flow using linear movement, and the material used to make components of the device, which allow them to be precisely machined. The tight tolerances achieved by the precise machining prevents red blood cells from moving between device components and thus becoming damaged, as well as minimizes the number of components in the device at least because seals do not have to be included. In addition to providing a slower pump speed that corresponds more closely to heart rates in the normal range for recipients, the linear motion of the shuttle further prevents red blood cell damage since it does not create shear forces.

As used herein, the terms "cylinder," "housing," and "cylindrical housing" are used interchangeably throughout, and the terms "cylinder bore," "cylinder head," and "chamber" are used interchangeably throughout. It should be appreciated, however, that the housing may, but need not, be cylindrical. Furthermore, use of the term "about" generally means within ±5% of a value or measurement.

Embodiments are set forth herein that provide a reliable and effective implantable ventricular assist device that utilizes a single acting positive displacement shuttle pump. Further embodiments are also set forth herein that provide a reliable and effective implantable ventricular assist device that utilizes a double acting positive displacement shuttle pump. Still further embodiments that provide a reliable and effective implantable artificial heart utilizing a double acting positive displacement shuttle pump are set forth herein.

The devices for pumping blood described herein generally include a cylindrical housing comprising an exterior, a plurality of ports, a first end, and a second end, where the first and second ends define a chamber therebetween. A shuttle is contained within the chamber, where the shuttle comprises an outer sleeve defining a hollow interior, and one or more channels longitudinally extending along the outer sleeve. The chamber may be a fixed-volume chamber such that the shuttle moving within the chamber defines two separate variable volume portions. The devices may also include a magnetic actuation system operable to effect linear and rotational motion to the shuttle, where the linear motion of the shuttle pumps blood into and out of the chamber according to a pumping cycle, and the rotational motion of the shuttle selectively directs the flow of blood through the plurality of ports. A biocompatible coating may also be provided on the housing exterior. The device may be a ventricular assist device or an artificial heart.

The housing, the shuttle, or both, may be made from a ceramic material or may comprise a ceramic material. Exemplary ceramic materials may include sapphire, synthetic variants of sapphire, zirconia, or synthetic variants of zirconia.

A manifold that helps to direct the flow of blood may be associated with the cylindrical housing. The manifold may be integrally formed with the housing or coupled thereto. For example, the manifold may be coupled to the housing using an attachment mechanism, such as a strap or strip of material. The strap or strip may be secured around the housing by a latch or other suitable fastening component.

When included as part of an artificial heart device, the manifold may include a first and second inlet, and a first and second outlet, where the first and second inlets and the first and second outlets are in fluid communication with corresponding ports of the plurality of ports. The first and second inlets of the manifold may be spaced about 90 degrees apart upon the exterior of the cylindrical housing. Likewise, the first and second outlets of the manifold may be spaced about 90 degrees apart upon the exterior of the cylindrical housing.

For ventricular assist devices, the manifold may include a single inlet and a single outlet, both of which may be in fluid communication with corresponding ports of the plurality of ports. Here the inlet and the outlet of the manifold may be spaced about 90 degrees apart upon the exterior of the cylindrical housing.

The housing and the shuttle components of the device will typically have a minimal clearance gap between them. For example, the clearance gap may be less than about 5.0 µm, less than about 4.0 µm, or less than about 3.0 µm. In some instances, the clearance gap may range from about 2.0 µm to about 4.0 µm. The clearance gap may generally be sized to prevent the passage of red blood cells between the housing and the shuttle, thereby eliminating the need to include seals within the device.

The shuttle of the devices disclosed herein may include a hollow cylindrical sleeve and end caps at each end of the sleeve. The shuttle may have a length and a diameter, and one or more channels extending along the outer surface of the sleeve. Shuttle diameters may range from about 3.5 cm to about 4.5 cm. The shuttle length may range from about 5.0 cm to about 6.0 cm.

Additionally, the one or more channels may have one open end and one closed end. Channel lengths may be between about 4.0 cm and about 5 cm. The depth of the one or more channels may be between about 0.5 cm and about 0.6 cm. In general, the channels may be formed without any square edges, and may solely include radiused edges.

Movement of the shuttle within the housing may generally be achieved using a magnetic actuation system. The magnetic actuation system may include a plurality of magnets disposed within the hollow interior of the outer sleeve, a plurality of linear motor coils encircling the cylindrical housing, and a plurality of rotational coils disposed at the first and second ends of the cylindrical housing. Alternatively, the magnetic actuation system may include a plurality of magnets disposed within the hollow interior of the outer sleeve, a plurality of linear motor coils encircling the cylindrical housing, and a permanent magnet disposed within each of the first and second ends of the cylindrical housing.

A controller may be operably coupled to the magnetic actuation system and may be configured to automatically control the pumping cycle using a feedback loop. Here one or more pressure sensors may be operably connected to the controller. Blood pressure data received by the controller from the one or more pressure sensors may be used to automatically adjust the magnetic actuation system to increase or decrease the rate or speed of the pumping cycle. Manual adjustment of the pumping cycle may also be made by a device recipient or a physician. In some instances, the controller may include a Bluetooth system operable to transmit information about the pump device to an external device such as a computer, cell phone, or hand-held portable controller. In other instances, the controller may include a telemetry system operable to transmit information about the device to an external device and receive information from the external device. One or more rechargeable batteries may be included with the pump devices. The batteries may be implanted in any suitable location of the recipient's body. For example, a first battery may be implanted on the left side of the recipient just above the hip or approximately in that area, and a second battery may be implanted on the right side of the recipient just above the hip or approximately in that area.

Some devices for pumping blood described herein may include a cylindrical housing comprising an exterior, first and second inlet ports, first and second outlet ports, a first end, and a second end, the first and second ends defining a chamber therebetween, a shuttle within the chamber, the shuttle comprising an outer sleeve defining a hollow interior containing a plurality of magnets therein, and one or more channels longitudinally extending along the outer sleeve, and a magnetic actuation system operable to effect linear and rotational motion to the shuttle, where the linear motion of the shuttle pumps blood into and out of the chamber according to a pumping cycle, and the rotational motion of the shuttle selectively directs the flow of blood through the first and second inlet ports and the first and second outlet ports. Here the device may be an artificial heart. The devices may further include a manifold associated with the cylindrical housing, the manifold comprising a first and second inlet, and a first and second outlet, wherein the first and second inlets and the first and second outlets are in fluid communication with corresponding ports of the first and second inlet ports and the first and second outlet ports.

Other exemplary artificial hearts described herein may include a cylindrical housing comprising a plurality of ports; a shuttle within the cylindrical housing, where the shuttle is made from a sapphire material; and a clearance gap between the housing and the shuttle, where the clearance gap is sized to prevent passage of red blood cells. The clearance gap may be between about 2.0 µm to about 4.0 µm.

Furthermore, some devices for pumping blood described herein may include a cylindrical housing comprising an exterior, a single inlet port, a single outlet port, a first end, and a second end, the first and second ends defining a chamber therebetween, a shuttle within the chamber, the shuttle comprising an outer sleeve defining a hollow interior containing a plurality of magnets, and one or more channels longitudinally extending along the outer sleeve, a magnetic actuation system operable to effect linear and rotational motion to the shuttle, where the linear motion of the shuttle pumps blood into and out of the chamber according to a pumping cycle, and the rotational motion of the shuttle selectively directs the flow of blood through the single inlet port and the single outlet port. Here the device may be a ventricular assist device. The devices may further include a manifold comprising a single inlet and a single outlet, both of which are in fluid communication with a corresponding single inlet port and a corresponding single outlet port.

Methods for pumping blood in a recipient are further described herein. The methods may generally include linearly reciprocating a shuttle contained within a housing to simultaneously move blood into and out of the housing according to a pumping cycle, the housing comprising a plurality of ports; and rotating the shuttle to selectively direct the movement of blood into and out of the plurality of ports. In some instances, the method also includes implanting the housing in the recipient. Implanting may comprise coupling a first port of the plurality of ports to the aorta of the recipient, and coupling a second port of the plurality of ports to the left ventricle of the recipient. Alternatively, implanting may include coupling a first port of the plurality of ports to the aorta of the recipient, coupling a second port of the plurality of ports to the pulmonary artery of the recipient, coupling a third port of the plurality of ports to the inferior vena cava and the superior vena cava of the recipient, and coupling a fourth port of the plurality of ports to the pulmonary vein of the recipient. The pumping cycle of the devices may be automatically adjusted based on the blood pressure of the recipient, or manually adjusted by the recipient or a physician.

Some of the methods described herein may include implanting a housing comprising a plurality of ports in the recipient, wherein implanting comprises coupling a first port of the plurality of ports to the aorta of the recipient, coupling a second port of the plurality of ports to the pulmonary artery of the recipient, coupling a third port of the plurality of ports to the inferior vena cava and the superior vena cava of the recipient, and coupling a fourth port of the plurality of ports to the pulmonary vein of the recipient; linearly reciprocating a shuttle contained within the housing to simultaneously move blood into and out of the housing according to a pumping cycle; and rotating the shuttle to selectively direct the movement of blood into and out of the plurality of ports.

Other methods described herein may include implanting a housing comprising a plurality of ports in the recipient, wherein implanting comprises coupling a first port of the plurality of ports to the aorta of the recipient, and coupling a second port of the plurality of ports to the left ventricle of the recipient; linearly reciprocating a shuttle contained within the housing to simultaneously move blood into and out of the housing according to a pumping cycle; and rotating the shuttle to selectively direct the movement of blood into and out of the plurality of ports.

Methods for treating heart failure are further described herein. The methods may generally include implanting a housing into a recipient, the housing comprising a shuttle; linearly reciprocating the shuttle to simultaneously move blood into and out of the housing; and rotating the shuttle to direct the flow of blood into and out of the housing, where linearly reciprocating and rotating the shuttle generates a pumping cycle of the housing. Here again, the housing and shuttle may function as a ventricular assist device or as an artificial heart. The types of heart failure that may be treated include without limitation, heart failure attributed to left-sided heart failure, right-sided heart failure, biventricular heart failure, cardiomyopathy, or an infection.

More specifically, the various embodiments set forth herein may utilize a cylinder having closed opposed ends and a cylinder bore extending therebetween. Within the cylinder bore, a shuttle having a generally cylindrical shape and supporting a plurality of magnets may be freely movable. Input and output ports may be formed in the cylinder at the mid-points of the cylindrical bore to provide coupling to a recipient's circulatory system as required for ventricular assist device or artificial heart operation. A set of linear motor coils may be disposed upon the outer surface of the cylinder and may be configured to interact with the magnets supported within the shuttle. Electrical signals may be applied to the linear motor coils by a controller to drive the shuttle between the closed ends of the cylinder in a reciprocating motion. The outer surface of the shuttle may define one or more blood flow channels, each of which may be open at one end and closed at the other end. Additionally, magnetic components may be provided to rotate the shuttle prior to each reciprocating motion to align the selected blood flow channels with selected input and output ports. By appropriate rotational positioning of the shuttle and linear movement thereof once rotationally positioned, blood may be drawn into one end of the cylindrical housing after which rotation of the shuttle may align the selected blood flow channels such that returning linear motion of the shuttle may displace the accumulated blood therein outwardly through the output port.

In a single acting embodiment of the pump device, blood may be drawn into and pumped from one end of the cylindrical housing as the shuttle reciprocates. In double acting embodiments of the pump device, blood may be simultaneously drawn into the cylinder at one end and expelled from the cylinder at the other end as the shuttle reciprocates. For both single acting and double acting embodiments of the pump device, the reciprocating motion and rotational motion of the shuttle may be sequenced to draw successive volumes of blood into the cylinder through the input port(s) and displace it outwardly from the cylinder through the output port(s).

BRIEF DESCRIPTION OF THE DRAWINGS

FIGS. 2A, 2B, 2C, 3A, 3B, and 3C taken together are sequential section views of an exemplary single acting ventricular assist device illustrating a complete operative cycle thereof.

FIGS. 11A, 11B, 11C, 12A, 12B, 12C, 13A, 13B, 13C, 14A, 14B, 14C, 15A, 15B, 15C, 16A, 16B, 16C, 17A, 17B, and 17C taken together are sequential section views of an exemplary artificial heart illustrating a complete operative cycle thereof.

FIG. 20A is a cross-sectional view of an exemplary device for pumping blood.

FIG. 20B is a cross-sectional view of the device in FIG. 20A with the housing, shuttle, and end caps shown separately.

FIG. 26A provides a cross-sectional view of the exemplary magnet; FIG. 26B shows a cross-sectional view of the magnet of FIG. 26A within a shuttle; and FIG. 26C illustrates stacking of several of the magnets of FIG. 26A to form a magnet stack having the shape of a channel.

DETAILED DESCRIPTION

Figure 1:
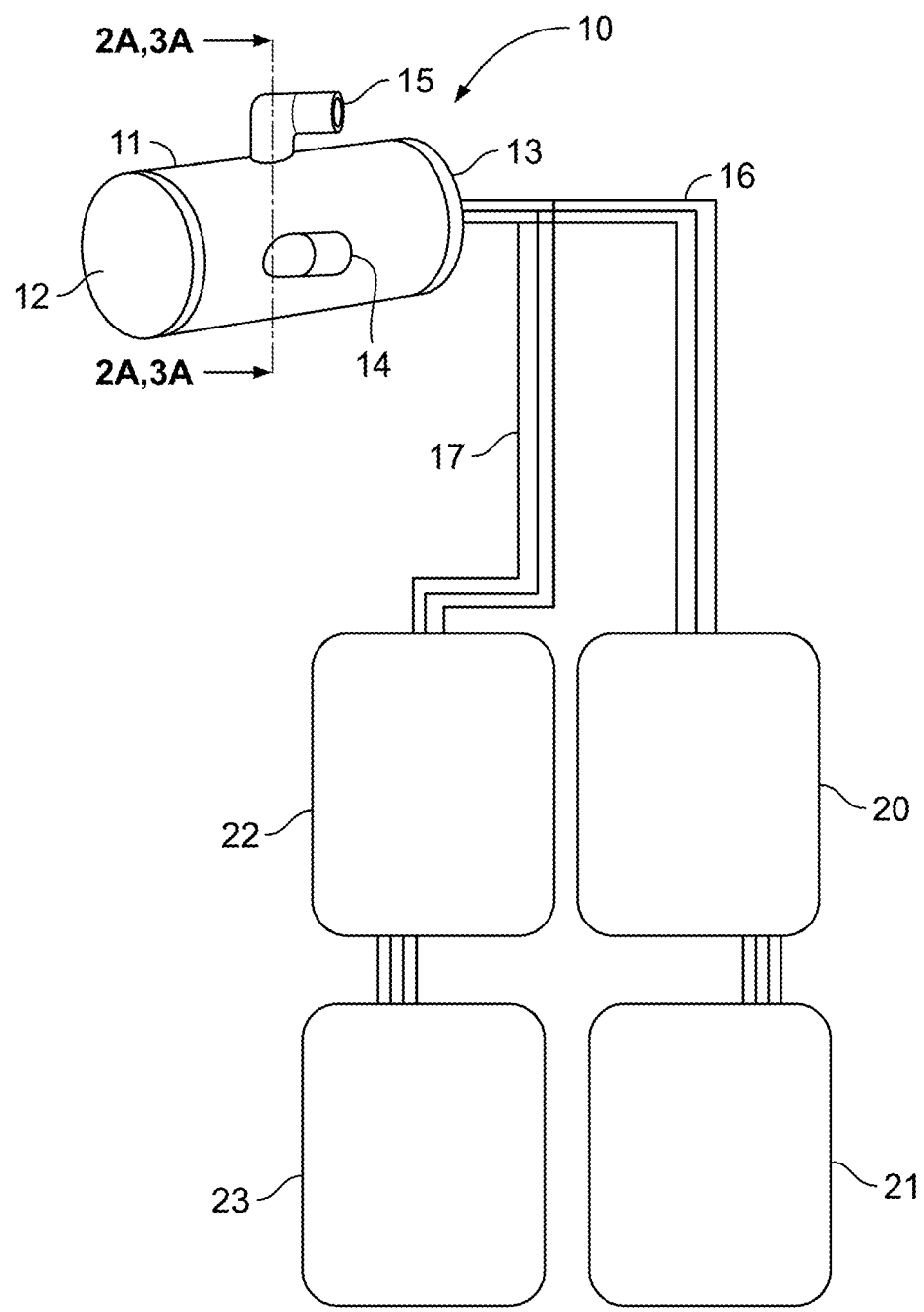
FIG. 1 is a perspective view of an exemplary single acting ventricular assist device coupled to a redundant set of controllers and battery power supplies.

Described herein are devices and methods for pumping blood in a patient in need of circulatory assistance or a replacement heart. Instead of providing a temporary solution for these patients (recipients), the devices may be permanently implanted. As stated above, there are several features of the devices described herein that enable the devices to provide permanent solutions for these patients, such as, for example the lack of an impeller that must rotate at high speed to efficiently pump blood, a shuttle that primarily generates blood flow using linear movement, and the material used to make components of the device, which allows them to be precisely machined and thus to achieve tight tolerances between components. The tight tolerances achieved may prevent (or substantially reduce the quantity of) red blood cells from moving between device components and thus becoming damaged, and may minimize the number of components in the device. For example, the tight tolerances achieved in the devices may entirely eliminate the need for seals in the devices. The linear motion of the shuttle may further prevent red blood cell damage at least because it does not create shear forces. Further, because of its efficiency, it moves blood at a slower natural speed thereby also preventing red blood cell damage.

Devices for Pumping Blood

The devices for pumping blood described herein may function as a ventricular assist device or an artificial heart. The devices may generally include a housing comprising an exterior, a plurality of ports, a first end, and a second end. The first and second ends may define a chamber therebetween, and a shuttle may be positioned within the chamber. The shuttle may comprise an outer sleeve defining a hollow interior and one or more channels longitudinally extending along the outer sleeve. The devices may further comprise a magnetic actuation system, which may be operable to effect linear and rotational motion to the shuttle. The linear motion of the shuttle may serve to pump blood into and out of the chamber according to a pumping cycle, and the rotational motion of the shuttle may serve to selectively direct the flow of blood through the plurality of ports.

Housing

As mentioned above, the devices described herein may generally comprise a housing, for example, a cylindrical housing, or a housing having an elliptical or a rectangular cross-sectional shape. The housing may generally comprise a first end and a second end, which may be end caps used to enclose the housing and form a chamber therewithin. The chamber may be a fixed-volume chamber such that a shuttle moving within the chamber defines two separate variable volume portions. The housing may further comprise a plurality of ports (e.g., one or more inlet ports, one or more outlet ports), which may allow movement of blood into and out of the housing. The ports may be included in any suitable area of the housing, e.g., centrally and/or at the ends of the housing. Furthermore, the ports may be positioned to correspond with the spacing of inlets and outlets of a manifold, as further described below.

The size of the ports may vary depending on such factors as the size of the housing, the intended recipient, and/or the number of ports to be included in the housing. For example, the diameter of the ports may vary depending on the size of the housing. For example, the diameter of the ports may range from about 0.20 cm to about 0.60 cm. When the device is used as a ventricular assist device, two ports may be included, one for movement of blood into the housing (an inlet port), and one for movement of blood out of the housing (an outlet port). When the device is used as an artificial heart, four ports may be included, two for moving blood into the housing (first and second inlets), and two for moving blood out of the housing (first and second outlets). However, any suitable number of ports may be employed. For example, 6, 8, or 10 ports may be included in the housing.

The housing may be made from or may comprise a ceramic material. Exemplary ceramic materials may include sapphire, synthetic variants of sapphire, zirconia, synthetic variants of zirconia, and the like. The materials may be ground and polished to achieve the lowest coefficient of friction possible. In some instances, the housing may be made from metals such as stainless steel, alloys of stainless steel, titanium, or alloys of titanium. In other instances, the housing may be made from or comprise a plastic material, or other suitable biocompatible materials.

In some embodiments, the housing may comprise a coating on an exterior surface thereof. The coating may be made from any suitable biocompatible polymer. For example, polymers such as silicone, polyethylene, acrylic resins, polyurethane, and polypropylene may be used. However, when the housing is made from a ceramic material, for example, sapphire or zirconia, a coating may not be needed because these materials are biocompatible and non-immunogenic.

The dimensions of the housing may vary according to the person receiving the device, for example, a child or an adult, or the size of the device. In general, larger housings may be suitable for adult recipients and smaller housings may be suitable for pediatric recipients. The length of the housing may range from about 5.0 cm to about 10 cm, including all values and sub-ranges therein. For example, the length of the housing may be about 5.0 cm, about 6.0 cm, about 7.0 cm, about 8.0 cm, about 9.0 cm, or about 10 cm. In variations in which a cylindrical housing is used, the diameter of the cylindrical housing may range from about 1.5 cm to about 2.5 cm, including all values and sub-ranges therein. For example, the diameter of the cylindrical housing may be about 1.5 cm, about 2.0 cm, or about 2.5 cm.

The housing may be enclosed on each end with an end cap. The radius of curvature of the end cap may generally be configured so that its inner surface (i.e., the housing face, which faces the chamber) is not flush with the outer surface of the shuttle end cap (i.e., the shuttle face). More specifically, the curvature of the housing face may have a greater radius of curvature than that of the shuttle face. Alternatively, the housing face may be flat and the shuttle face curved. As a result, the shuttle face may be driven against the housing face without conforming to the housing face, thereby avoiding creation of a vacuum attachment therebetween that could otherwise impede movement of the shuttle face away from the housing face or damage red blood cells. When the housing face is curved, it may have a radius of curvature of from about 9 cm to about 10 cm, and for example, of about 9.86 cm (3.88 in).

Referring to FIGS. 20A and 20B, a partial cross-sectional view of an exemplary pump device 200 including a housing or cylinder 202 is shown. Although housing 202 is described as being cylindrical, other shapes may be employed. Housing 202 may include a plurality of ports 204, and end caps 206, 208 at a first end 210 and a second end 212 of the housing 202 that define a chamber 213 therebetween.

Shuttle

The devices described herein may generally comprise a shuttle disposed within the chamber of the housing. The shuttle, which functions as a piston, may be linearly translated within the chamber to pump blood into and out of the housing. The shuttle may define two separate variable volume portions of a fixed-volume chamber as it moves back and forth within the chamber. The shuttle may comprise an outer sleeve, which may have a hollow interior, and first and second shuttle end caps positioned at opposite ends of the outer sleeve. The outer sleeve may be cylindrical.

The shuttle may comprise one or more magnets (shuttle magnets) positioned and held within the hollow interior of the sleeve. The magnets may be used in conjunction with the magnetic actuation systems, described in more detail herein, for actuating motion of the shuttle. In some variations, the shuttle may comprise a single magnet, while in other variations, the shuttle may comprise a plurality of magnets (e.g., two, three, four, five, six, seven, or more). In other variations, the shuttle may include a first rotational motion magnet at one end adjacent a first linear motion magnet together with a second rotational motion magnet adjacent a second linear motion magnet at the opposite end.

Figure 26C:
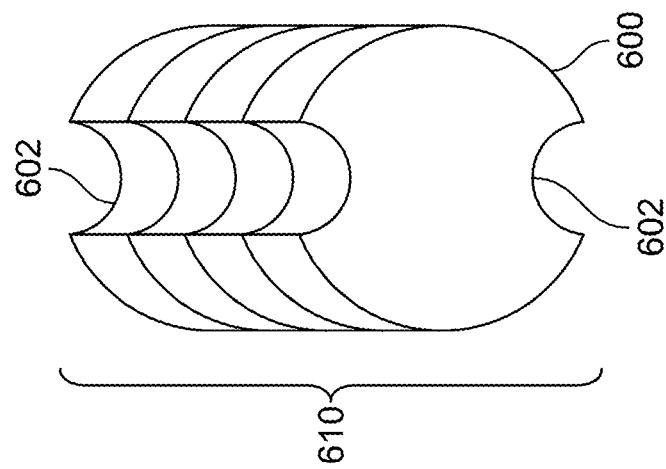
FIGS. 26A to 26C depict an exemplary magnet that corresponds to the shape of the channels in a shuttle.
Figure 26B:
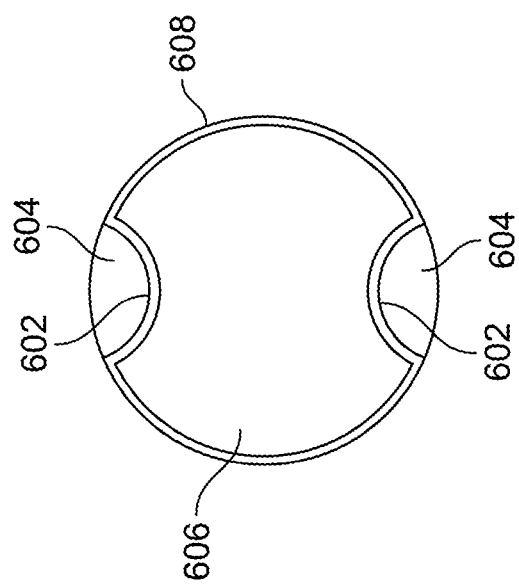
Figure 26A:
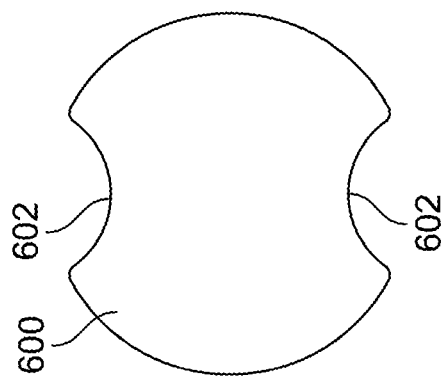

In some instances, the shuttle magnets may be electromagnets. In some variations, the shuttle magnets may be permanent rare-earth magnets such as neodymium magnets. In these variations, the neodymium magnets may be arranged alternatively, for example, NS SN NS SN NS, if five magnets are employed (where "S" refers to the south pole of the magnet and "N" refers to the north pole of the magnet). The south poles of each adjacent magnet may face one another and the north poles of each adjacent magnet may face one another. In variations in which a single magnet may be used, the single magnet may comprise a ceramic material that may be magnetized to create the same arrangement. The one or more shuttle magnets may be cylindrical. In other variations, the shape of the shuttle magnets may correspond to the shape of the channel in the outer sleeve of the shuttle. For example, referring to FIGS. 26A to 26C, magnets may be shaped to match or correspond to the shape of channels in a shuttle, such as, for example, the shape of a shuttle having two channels. Thus, as shown in the FIG. 26A, magnet 600 may be shaped to include arc-shaped or radiused cut-outs 602 that correspond to the shape of channels 604 (see cross-sectional view of shuttle 606 in a housing 608, as shown in FIG. 26B). The shape of the magnets 600 corresponding to the shape of the channels 604 is further illustrated when a plurality of magnets 600 are provided in a magnet stack 610, as shown in FIG. 26C.

The shuttle may further comprise one or more channels that may be formed in the outer sleeve. The one or more channels may longitudinally extend along the outer sleeve, but may be oriented in any suitable direction that permits blood flow to be selectively directed into and out of the housing. The shuttle may be configured to rotate to align the channels with certain ports of the housing to selectively direct blood through the ports. For example, the shuttle may be rotated about 90 degrees to selectively direct blood from the inferior and superior vena cava into inlet ports of the housing that is fluidly coupled thereto, selectively direct blood from the pulmonary vein into an inlet port of the housing that is fluidly coupled thereto, selectively direct blood out of the housing into the pulmonary artery via an outlet port fluidly coupled thereto, or selectively direct blood out of the housing into the aorta via an outlet port fluidly coupled thereto. In some embodiments, the shuttle selectively directs blood from the inferior and superior vena cava into the housing via inlet ports while simultaneously selectively directing blood out of the housing to the pulmonary artery via outlet ports. In other embodiments, the shuttle selectively directs blood from the pulmonary vein into the housing via the inlet port while simultaneously directing blood out of the housing into the aorta via the outlet port.

The dimensions of the shuttle will typically vary according to the dimensions of the housing. The shuttle may have a length ranging from about 5.0 cm to about 6.0 cm, including all values and sub-ranges therein. For example, the shuttle length may be about 5.0 cm, about 5.5 cm, or about 6.0 cm. In variations comprising a cylindrical outer sleeve, the shuttle may have a diameter ranging from about 3.5 cm to about 4.5 cm, including all values and sub-ranges therein. For example, the shuttle diameter may be about 3.5 cm, about 4.0 cm, or about 4.5 cm.

The shuttle may be made from, or may comprise, the same material(s) as the housing, and may generally be capable of being precisely machined so that seals (e.g., O-rings) need not be included in the device. For example, the housing, the shuttle, or both, may generally be made from a material that can be precisely machined. In one embodiment, the material may be a ceramic material. Exemplary ceramic materials may include without limitation, sapphire or synthetic variants thereof, and zirconia or synthetic variants thereof. In one embodiment, the housing may be made, entirely or partially, from a sapphire material. In another embodiment, the shuttle may be made, entirely or partially, from a sapphire material. In yet a further embodiment, both the housing and the shuttle may be made, entirely or partially, from a sapphire material. In other embodiments, the shuttle and the housing may be comprised of materials such as titanium, alloys of titanium alloys, stainless steel, alloys of stainless steel, plastics, or other suitable biocompatible materials.

The ability to precisely machine the housing and the shuttle may allow for a close or tight fit between the components, and thus may minimize the clearance gap formed between the components (e.g., between the exterior surface of the shuttle and the interior surface housing (e.g., chamber)). In one embodiment, the clearance gap may be less than about 5.0 µm. In another embodiment, the clearance gap may be less than about 4.0 µm. In a further embodiment, the clearance gap may be less than about 3.0 µm. In yet further embodiments, the clearance gap may be from about 2.0 µm to about 4.0 µm, including all values and sub-ranges therein. In some embodiments, the clearance gap may be about 2.0 µm, about 2.5 µm, about 3.0 µm, about 3.5 µm, or about 4.0 µm. In other embodiments, the clearance gap may be sized to prevent passage of red blood cells between the interior surface of the housing and the exterior surface of the shuttle.

The shuttle may comprise one or more channels, which may extend longitudinally along the outer surface of the shuttle (i.e., the outer sleeve). Each channel of the plurality of channels may have one open end and one closed end to aid in the movement of blood into and out of the housing, as further described below. Furthermore, each channel of the plurality of channels may solely include radiused edges, which may prevent or minimize damage to red blood cells as they are pumped through the housing. The dimensions of the channels may vary with the dimensions of the shuttle. In general, the channels may have a length ranging from about 4.0 cm to about 5.0 cm, and a depth ranging from about 0.5 cm to about 0.6 cm. In some variations, the shuttle may comprise two channels. In these variations, the two channels may be arranged to be about 90 degrees apart on the surface of the shuttle, or arranged to be about 180 degrees apart on the surface of the shuttle.

Figure 21:
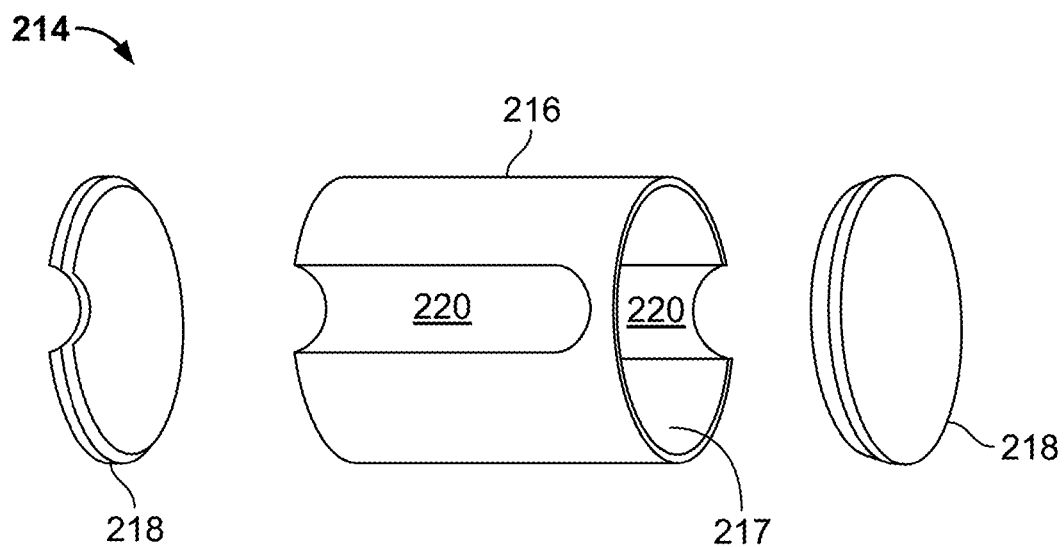
FIG. 21 depicts an assembly view of the shuttle.
Figure 22:
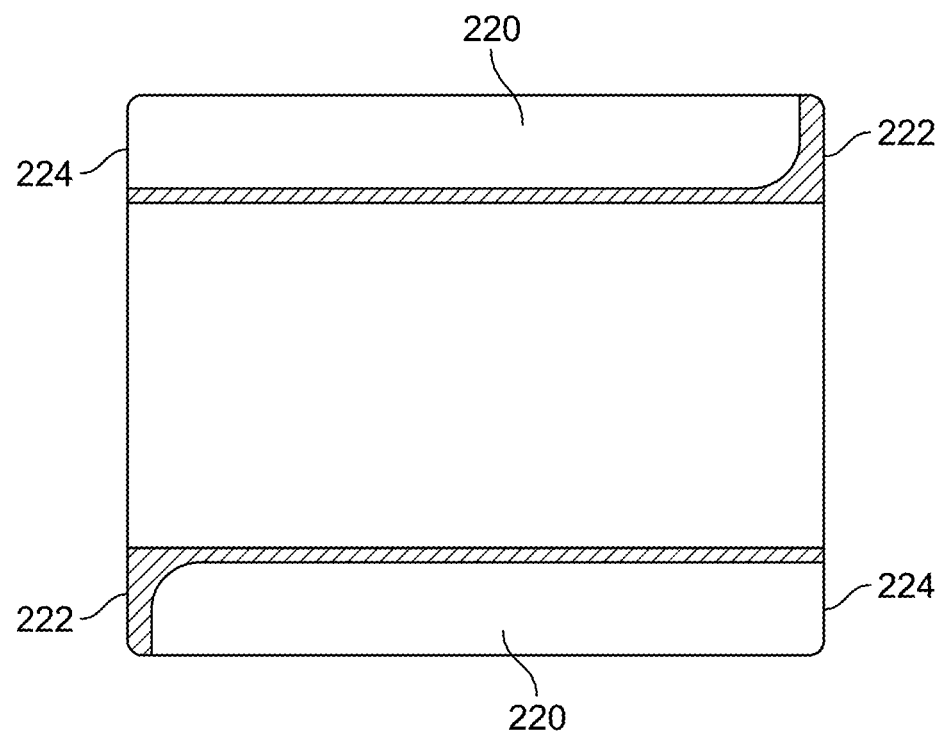
FIG. 22 is cross-sectional view of the channels in the shuttle showing the channels having one open end and one closed end.

Referring back to FIGS. 20A and 20B, shown there is a shuttle 214 positioned in the housing 202 of the pump device 200. As described herein, shuttle 214 may function as a piston that reciprocates back and forth to pump blood. Shuttle 214 includes an outer sleeve 216 defining a hollow interior 217 and a shuttle end cap 218 at each end of the sleeve 216, as better illustrated in FIG. 21. Channels 220 are also provided that extend longitudinally along the outer sleeve 216. Referring to FIG. 22, an expanded view of the channels 220 is shown having one closed end 222 and one open end 224. The closed and open ends help facilitate the flow of blood into and out of the housing, as further explained below.

Figure 23:
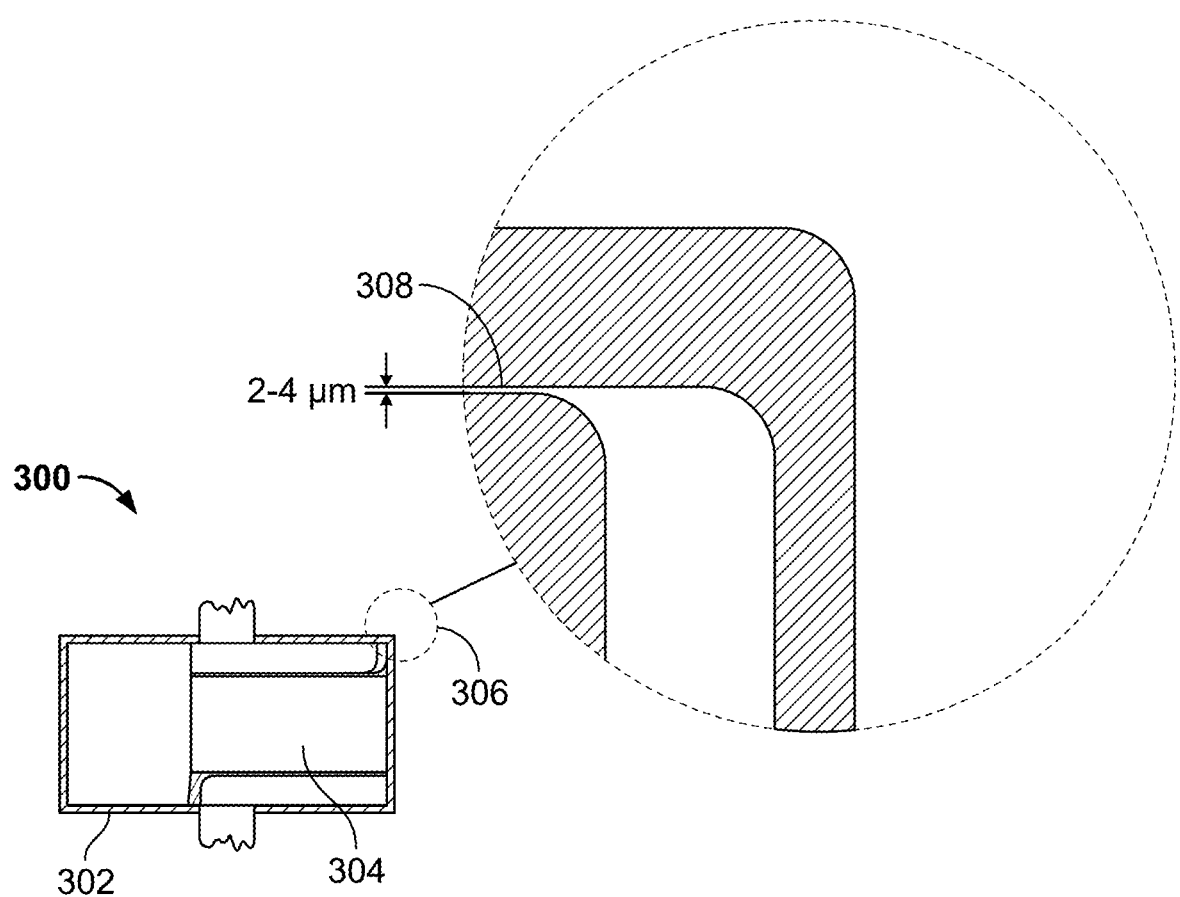
FIG. 23 provides a close-up view of the clearance gap between the shuttle and housing.

Referring to FIG. 23, an exemplary device 300 is depicted including a housing 302 and shuttle 304 contained within the housing 302. Circled area 306 is shown expanded to illustrate the small clearance gap 308 between the housing 302 and the shuttle 304. In this variation, the clearance gap may generally be between about 2 µm to about 4 µm.

The shuttle end cap (i.e., the shuttle face) may have a radius of curvature that is less than the housing face. As a result, the shuttle face may be driven against the housing face without conforming to the housing face, thereby avoiding creation of a vacuum attachment therebetween that could otherwise impede movement of the shuttle face away from the housing face. In some embodiments, the shuttle face has a radius of curvature ranging from about 2.54 cm (1.0 inch) to about 10.16 cm (4.0 in). In one embodiment, the shuttle face has a radius of curvature of about 8.05 cm (3.17 inch).

Referring to FIGS. 20A and 20B, a partial cross-sectional view of an exemplary pump device 200 including a housing or cylinder 202 is shown. Although housing 202 is described as being cylindrical, other shapes may be employed. Housing 202 may include a plurality of ports 204, and end caps 206, 208 at a first end 210 and a second end 212 of the housing 202 that define a chamber 213 therebetween.

As a result, the shuttle face may be driven against the housing face without conforming to the housing face, thereby avoiding creation of a vacuum attachment therebetween that could otherwise impede movement of the shuttle face away from the housing face. In one embodiment, the housing face may be curved. Here, the housing face may have a radius of curvature of about 9.86 cm (about 3.88 inch). In another embodiment, the housing face is flat, i.e., there is no radius of curvature.

Magnetic Actuation System

As previously mentioned, the shuttle within the chamber moves linearly to pump blood into and out of the chamber according to a pumping cycle, and rotates to selectively direct the flow of blood through the plurality of ports of the housing. Both the linear and rotational movement of the shuttle may be accomplished using a magnetic actuation system. In one embodiment, as further described below, the magnetic actuation system may comprise a plurality of linear motor coils encircling the housing and a plurality of rotational coils disposed at the first and second ends of the housing, each of which may interact with one or more magnets disposed within the interior of the outer sleeve (shuttle magnets). For example, the coils may be energized to create a magnetic field, which may interact with the shuttle magnets to effect shuttle movement. In some variations, a bank of three coils may generally be sufficient to form a complete drive unit for the magnetic actuation system. However, depending on the location of the ports, two three coil drive units may be used. In some embodiments, the magnetic actuation system may comprise a plurality of linear motor coils which may provide redundancy such that the device will still be functional should one coil fail.

The interaction between the plurality of shuttle magnets and the plurality of linear motion coils linearly reciprocates the shuttle, and the interaction between the plurality of shuttle magnets and the plurality of rotational coils rotates the shuttle. In another embodiment, which is also further described below, the magnetic actuation system may comprise a plurality of magnets disposed within the interior of the outer sleeve, a plurality of linear motor coils encircling the housing, and a permanent magnet disposed within each of the first and second ends of the housing. In this embodiment, the interaction between the plurality of shuttle magnets and the plurality of linear motion coils linearly reciprocates the shuttle, and the interaction between the plurality of shuttle magnets and the permanent magnets rotates the shuttle. Energization of the coils to create the magnetic fields that drive movement of the shuttle may be accomplished using three phase AC power, which can be switched in phase depending on the direction of drive/movement desired, and modulated in amplitude depending on the driving force required. In other embodiments, a 12 volt, 24 volt, or 48 volt DC power source may be used.

Generally, the magnetic field that is generated within the core of the drive coils may be proportional to the amount of current flowing in the coil. For example, when the coil is a flat donut, with wire wound around the circumference of the hole, a strong magnetic field may be generated within the hole when current flows in the coil, which may be represented as an arrow pointing out of the hole. The magnetic field direction, i.e., the arrow point, will be reversed when the direction of the current flow is reversed. This magnetic field interacts with the magnetic fields of the magnets in the shuttle, e.g., permanent Neodymium magnets, which may be extremely strong, for example, due to stacking. For example, in variations utilizing permanent magnets, the permanent magnets may be stacked so that N to N poles of adjacent magnets face one another, and S to S poles of adjacent magnets face one another. By appropriate manipulation of the current flows in the drive coils, the interacting magnetic fields may provide axial force in the appropriate direction, either repelling or attracting, as desired to drive the pumping action of the shuttle. The rotational force that rotates the shuttle may be generated by separate coils at each end of the housing, and may be activated by a pump controller independently of the linear magnetic drive.

Manifold

In some variations, the pumping devices may be used with or may comprise a manifold. For example, in these variations, the housing may be generally associated with a manifold, which may be configured to help direct the flow of blood to and from the housing and into and from the appropriate anatomy of the recipient (e.g., the inferior or superior vena cava, the pulmonary artery, the pulmonary vein, the aorta, or the left ventricle). Furthermore, the manifold may comprise one or more inlets and one or more outlets whereby the recipient's vasculature, left ventricle, or other appropriate anatomy may be connected to the housing. The inlets and outlets may be in fluid communication with corresponding ports of the plurality of housing ports. For example, when the device is a ventricular assist device, the manifold may comprise a single inlet and a single outlet, and when the device is an artificial heart, the manifold may comprise a pair of inlets (first and second inlets), and a pair of outlets (first and second outlets). When the manifold is part of or used with a ventricular assist device, the single inlet of the manifold may be in fluid communication with the left ventricle of a recipient, and the single outlet of the manifold may be in fluid communication with the aorta of the recipient. When the manifold is part of or used with an artificial heart, the first inlet may be in fluid communication with an inferior or superior vena cava of the recipient, and the second inlet may be in fluid communication with the pulmonary vein of the recipient. Furthermore, the first outlet may be in fluid communication with the pulmonary artery of the recipient, and the second outlet may be in fluid communication with the aorta of the recipient.

The spacing of the inlets and outlets of the manifold may generally be configured so that the inlets and outlets of the manifold align with corresponding ports of the plurality of ports in the housing. In some embodiments, for example, when the device is a ventricular assist device, the single inlet and the single outlet may be spaced about 90 degrees apart upon the exterior of the housing. In other embodiments, for example, when the device is an artificial heart, the first and second inlets of the manifold may be spaced about 90 degrees apart upon the exterior of the housing. Likewise, the first and second outlets of the manifold may be spaced about 90 degrees apart upon the exterior of the housing.

In some variations, the manifold may be formed integrally with the housing, while in other variations, the manifold may be formed separately from the housing and may be coupled to the housing, for example, using an attachment mechanism. For example, in some variations, the manifold may comprise an attachment mechanism in the form of a flexible strip or strap of material that is placed around the housing. The ends of the strip or strap may be secured together with a latch or other suitable fastening component. The manifold may be made from suitable biocompatible materials such as, for example, stainless steel or titanium. The attachment mechanism may be made from the same material as the manifold, or a different material (e.g., a flexible polymer such as polyethylene, polyethylene terephthalate, polyvinyl chloride, polypropylene, or polystyrene).

Figure 24A:
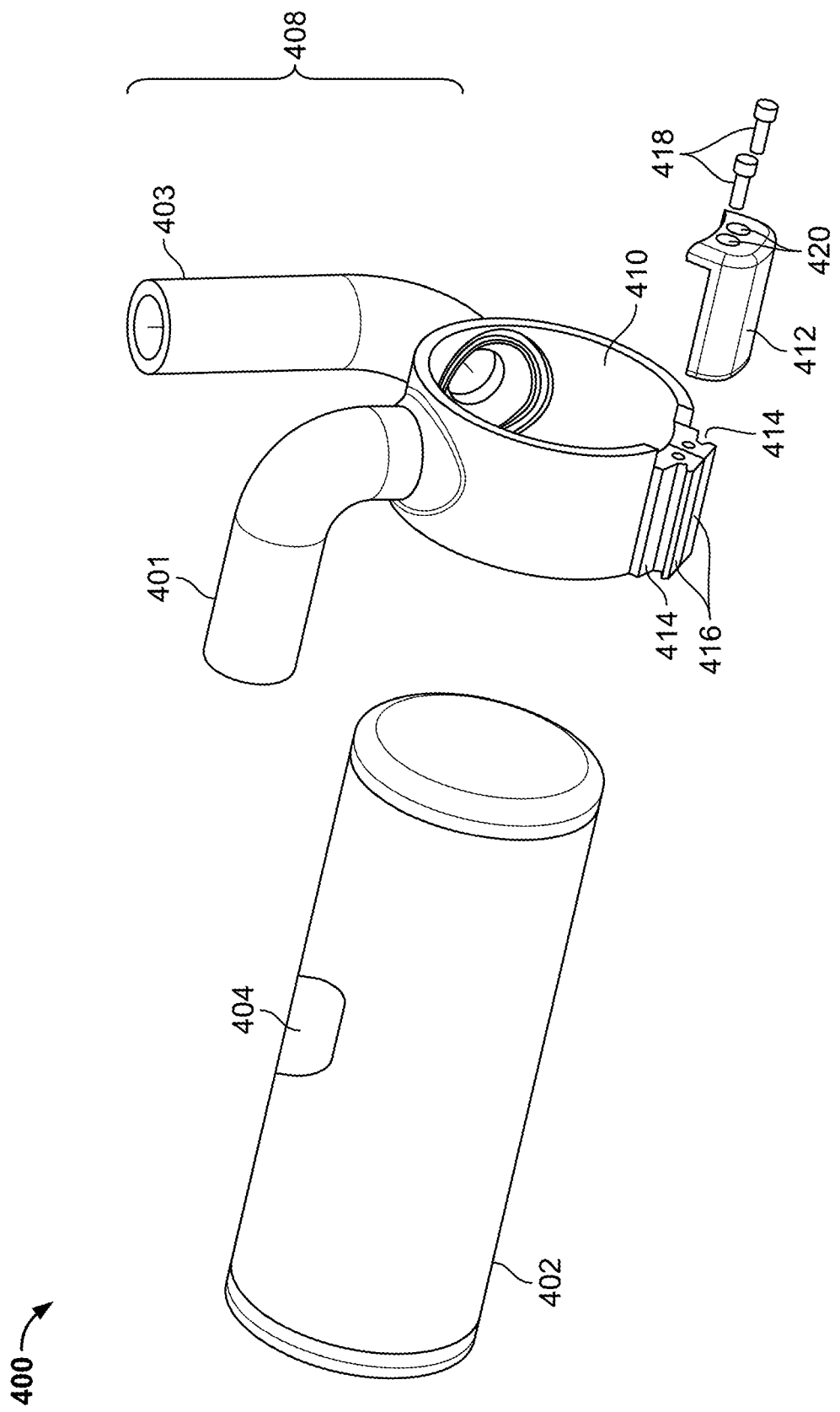
FIG. 24A depicts an assembly view of an exemplary ventricular assist device.
Figure 24B:
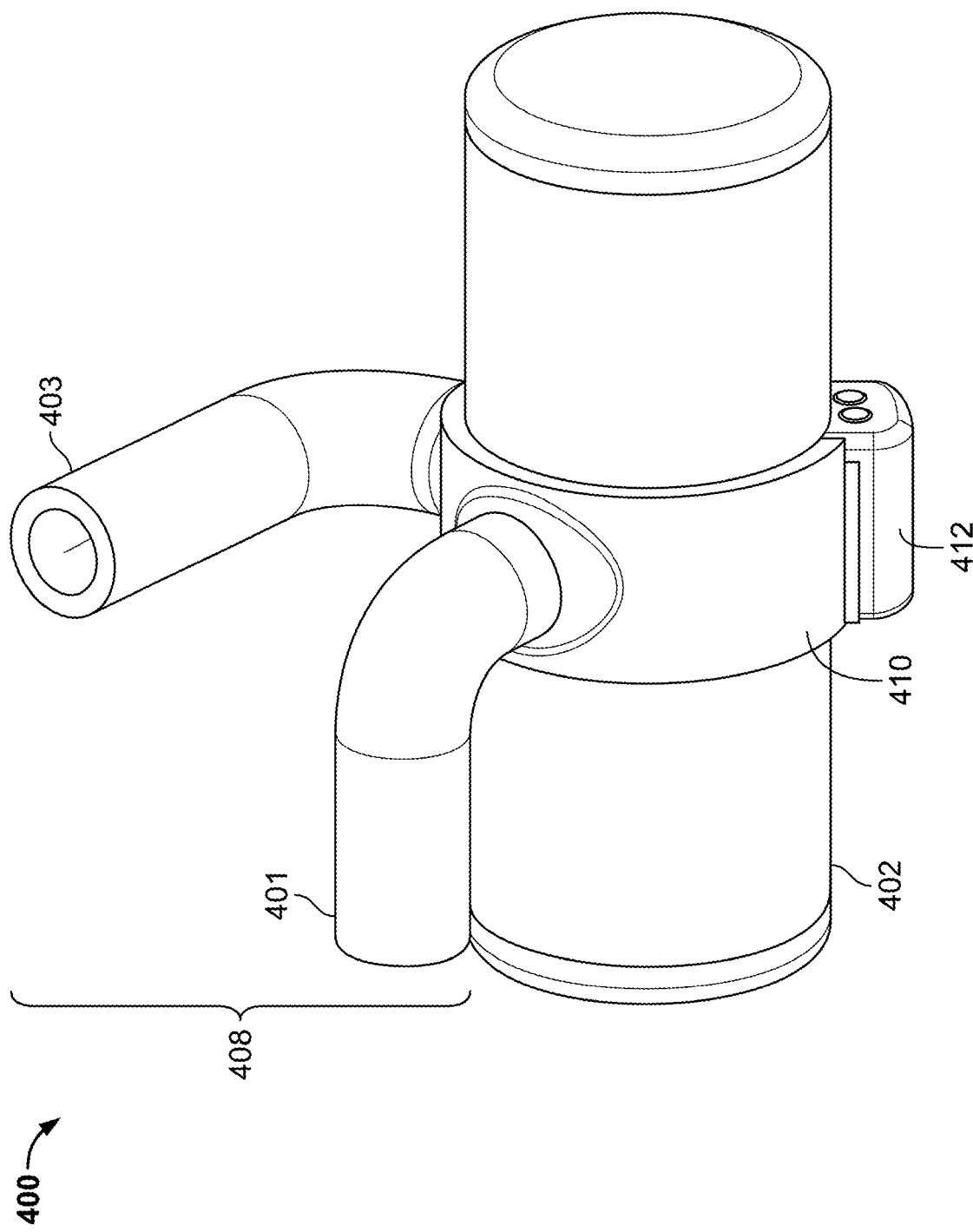
FIG. 24B shows the ventricular assist device of FIG. 24A with the manifold attached thereto.

Manifolds are generally also included in the pump devices described herein to help direct the flow of blood to and from the housing and into the appropriate anatomy of the recipient. When the device is a ventricular assist device, a single inlet of the manifold may be in fluid communication with the left ventricle of a recipient, and a single outlet of the manifold may be in fluid communication with the aorta of the recipient. The single inlet and single outlet of the manifold may be in fluid communication with a corresponding inlet port and outlet port of the housing. For example, as shown in FIGS. 24A and 24B, ventricular assist device 400 includes a housing 402 having an inlet port 404 and an outlet port (not shown). A manifold 408 may be coupled to the housing 402 by an attachment mechanism, i.e., strap 410. Strap 410 may be secured about the housing 402 using a fastener or plug 412. Upon fastening, inlet port 404 and outlet port may be aligned with a corresponding inlet 401 and outlet 403 of the manifold 408. The fastener 412 has grooves 414 that correspond with rails 416 provided at the ends of the strap 410. Set screws 418 may be placed into openings 420 to further secure attachment of the manifold 408 to the housing 402.

Figure 25A:
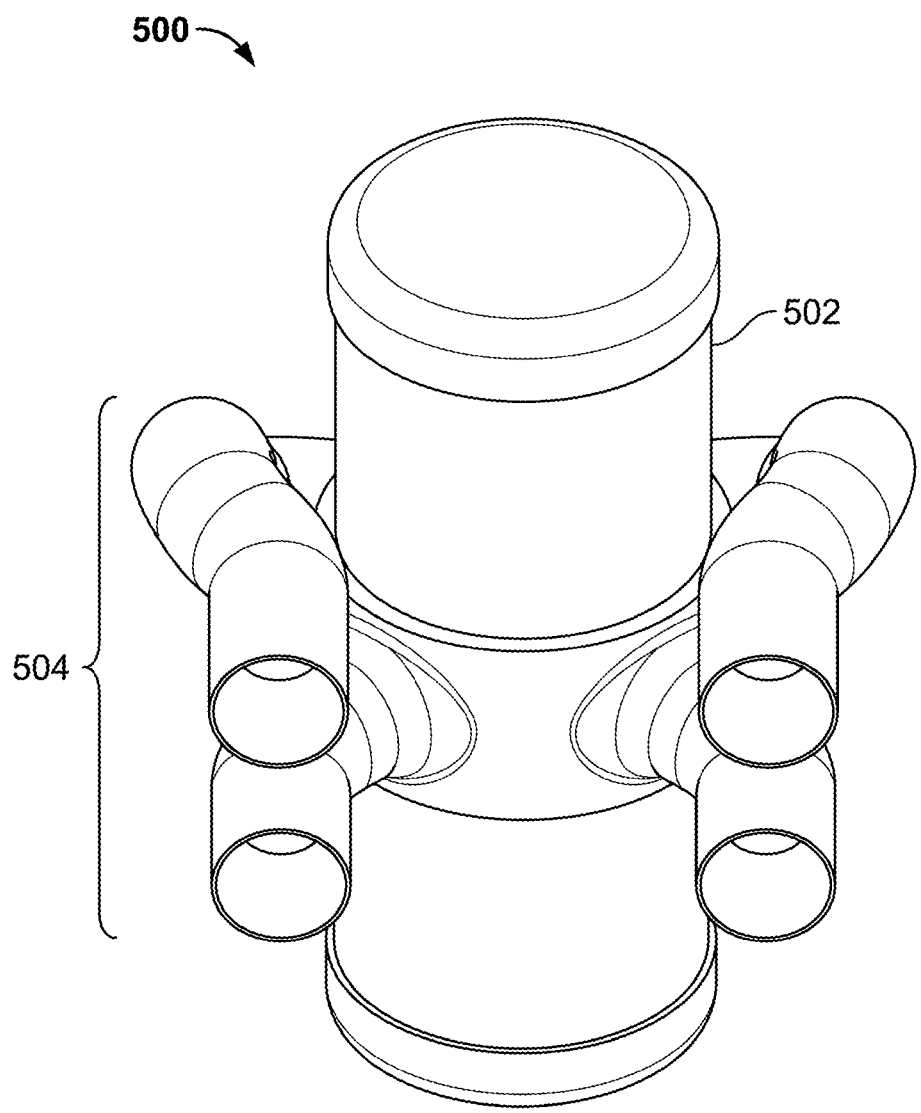
FIG. 25A depicts a perspective view of an exemplary artificial heart.
Figure 25C:
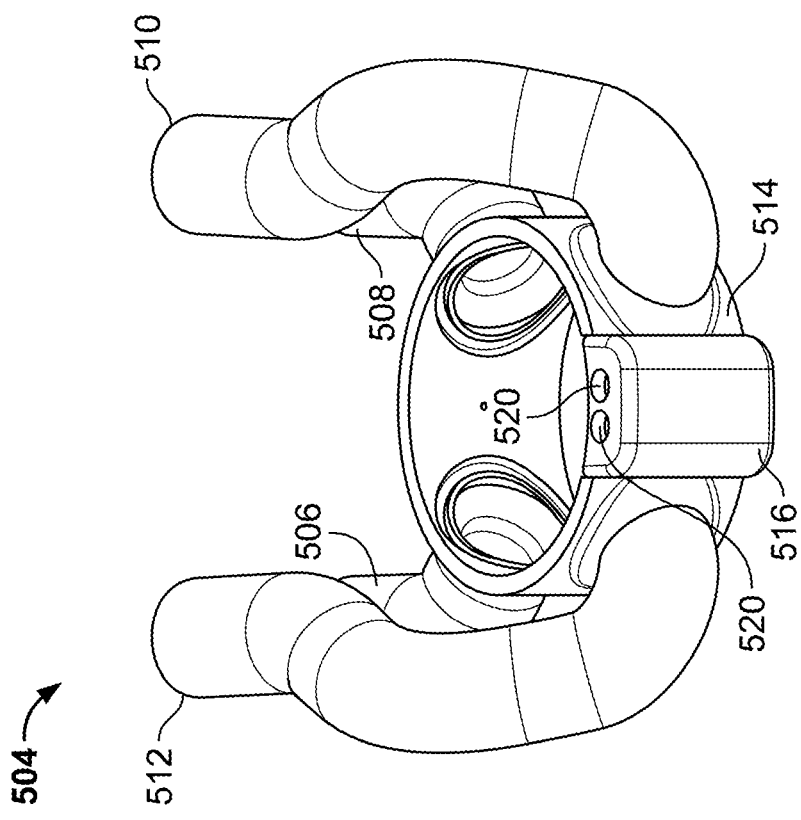
FIGS. 25B and 25C depict a perspective view of an exemplary manifold for the artificial heart shown in FIG. 25A in the unlatched (FIG. 25B) and latched (FIG. 25C) configurations.
Figure 25B:
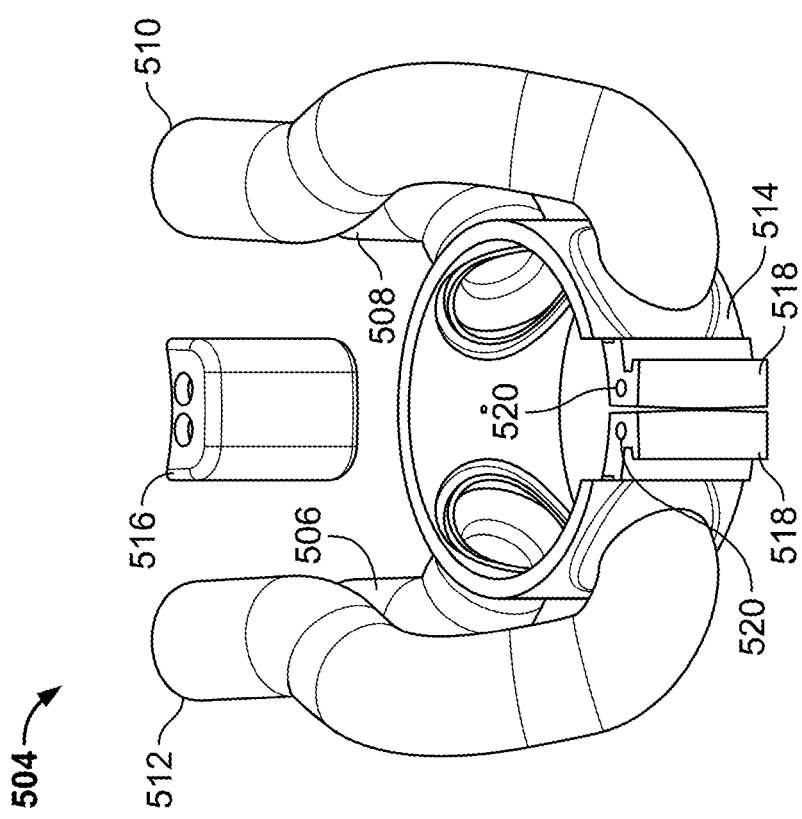

When the device is an artificial heart 500, as shown in FIG. 25A, the housing 502 may be coupled to the manifold 504 as shown in FIGS. 25B and 25C. Referring to FIG. 25B, manifold 504 includes a pair of inlets, first and second inlets 506, 508 and a pair of outlets, first and second outlets 510, 512. The first inlet 506 may be in fluid communication with an inferior or superior vena cava of the recipient, and the second inlet 508 may be in fluid communication with the pulmonary vein of the recipient. Furthermore, the first outlet 510 may be in fluid communication with the pulmonary artery of the recipient, and the second outlet 512 may be in fluid communication with the aorta of the recipient. The manifold 504 may be coupled to the housing 502 by an attachment mechanism, i.e., strap 514. Upon fastening, the inlets 506, 508 and outlets 510, 512 of the manifold may be in fluid communication with corresponding inlet ports (not shown) and outlet ports (not shown) of the housing 502. Strap 514 may be secured about the housing 502 using a fastener or plug 516. Similar to the ventricular assist device, the fastener 516 may have grooves (not shown) that correspond with rails 518 provided at the ends of the strap 514. Likewise, set screws (not shown) may be placed into openings 520 to further secure attachment of the manifold 514 to the housing 502.

The devices for pumping blood described herein may function as a ventricular assist device or an artificial heart. The devices are similar in structure, but the ventricular assist devices generally include a manifold having a single inlet and a single outlet, and are connected to a recipient's left ventricle and aorta. On the other hand, the artificial heart devices generally include a manifold having a first and second inlet, and a first and second outlet. The first and second inlets may be connected to the recipient's inferior and superior vena cava, and pulmonary vein, respectively, and the first and second outlets may be connected to the recipient's pulmonary artery and aorta, respectively. Additional details on the ventricular assist devices and artificial hearts are provided below.

Controller

The devices described herein may also include one or more controllers operably coupled to the magnetic actuation system, which may be configured to control the pumping cycle of the device, for example, control or adjust the speed of the pumping cycle (e.g., velocity of the shuttle and speed of rotation of the shuttle). In some variations, the devices may comprise two or more controllers (e.g., three, four, or more) such that the devices have redundancy should a controller cease operating. In addition to being operably coupled to the magnetic actuation system, the controller may be operably coupled to one or more sensors on the device. For example, in some variations, the device may comprise one or more pressure sensors (e.g., two, three, four, or more) that are operably coupled to the controller and that provide blood pressure data to the controller. The number of pressure sensors included with the device may be set to provide redundancy. When a pressure sensor detects blood pressure that is lower than a predetermined minimum blood pressure, the controller may automatically increase the speed of the pumping cycle. Similarly, when a pressure sensor detects blood pressure that is higher than a predetermined maximum blood pressure, the controller may automatically decrease the speed of the pumping cycle. The one or more pressure sensors may be positioned in any suitable location on the device, but typically are disposed near, within, or on a surface of, an outlet of the manifold. In one embodiment, for example, when the device is an artificial heart, four pressure sensors may be included on the device. The four pressure sensors may provide redundancy should one of the sensors stop operating. Here two sensors may be located on the each of the two outlets of the manifold.

The controller may be configured to be implanted in a recipient, or configured to remain external to the body. In both embodiments, the controller may include a Bluetooth system operable to transmit information about the pumping device to another device, for example, an external device such as a computer, a cell phone, a tablet, or other hand-held or portable device. In some embodiments, the controller may comprise a telemetry system operable to transmit information about the pumping device to another device, for example, an external device such as a computer, a cell phone, a tablet, or other hand-held or portable device, and receive information from that external device.

One or more rechargeable batteries may also be provided with the devices described herein. In some variations, the devices described herein may comprise two or more (three, four, or more) batteries, such that the devices have redundancy should a battery cease operating. In one embodiment, given that the batteries typically generate DC power, an inverter may be connected thereto to convert the DC power to the AC current required for the magnetic actuation system, controller, etc. The batteries may be charged via close range induction charging, where the charging device is worn by the recipient close to the implanted device. Additionally or alternatively, the batteries may be charged wirelessly using an antenna that receives a signal from a far field emitter, which is then converted to a signal capable of charging the battery. Far field charging may occur over distances up to about 20 feet from the emitter.

Ventricular Assist Devices

As discussed above, the ventricular assist devices described herein may generally include a cylindrical housing comprising an exterior, a single inlet port, a single outlet port, a first end, and a second end, where the first and second ends define a chamber therebetween. A shuttle may be provided within the chamber. The shuttle may comprise an outer sleeve defining a hollow interior containing a plurality of magnets, and one or more channels longitudinally extending along the outer sleeve. The ventricular assist device may further include a magnetic actuation system operable to effect linear and rotational motion to the shuttle, where the linear motion of the shuttle pumps blood into and out of the chamber according to a pumping cycle, and the rotational motion of the shuttle selectively directs the flow of blood through the single inlet port and the single outlet port. Additionally, the devices may include a manifold comprising a single inlet and a single outlet, both of which are in fluid communication with a corresponding single inlet port and a corresponding single outlet port.

FIG. 1 sets forth a perspective view of a single acting ventricular assist device 10. Ventricular assist device 10 is coupled to a controller 20, having a battery power supply 21, by a cable 16. Ventricular assist device 10 is further coupled to a backup controller 22, having a backup battery power supply 23, by a cable 17. The redundant set of controllers and battery power supplies improves the reliability of ventricular assist device 10. Ventricular assist device 10 together with controllers 20 and 22 and batteries 21 and 23 may be implanted within the patient recipient in their entirety, or alternatively, may be distributed with selected components remaining external to the patient recipient. Ventricular assist device 10 includes a generally cylindrical housing 11 having integrally formed ends 12 and 13. In one variation of its fabrication, housing 11, including ends 12 and 13, is formed of a biocompatible encapsulating material which is molded upon the operative structure set forth below (seen in FIG. 8). Housing 11 further supports an input coupler 14 and an output coupler 15 each operative in the manner set forth below to allow the transfer of blood to and from ventricular assist device 10.

In operation, ventricular assist device 10 is coupled to a patient circulatory system at a point at which it is desired to improve, or increase, the flow of blood. One common point of application of ventricular assist device 10 is shown below in FIG. 6 in an application commonly referred to as a left ventricular assist. Typically, ventricular assist device 10 is positioned to increase blood flow between selected portions of the patient circulatory system. As controller 20 provides operative electric signals to the drive apparatus (set forth below in FIG. 8) blood is drawn into ventricular assist device 10 through input coupler 14 and, thereafter, pumped outwardly through output coupler 15.

FIGS. 2A through 2C together with FIGS. 3A through 3C set forth sequential diagrams illustrating an operative cycle of ventricular assist device 10. It will be noted that the FIGS. shown are simplified to more clearly illustrate and understand the operative cycle of ventricular assist device 10. Thus, it will be understood that certain operative structure has been omitted from FIGS. 2A through 2C as well as FIGS. 3A through 3C to avoid unduly cluttering the FIGS. and to more readily understand the operation of ventricular assist device 10. With temporary reference to FIGS. 8, 9 and 10, it will be seen that ventricular assist device 10 is driven in a linear motion by a plurality of linear motor coils encircling the cylinder together with permanent magnets disposed within the interior of the shuttle. In addition, it will be equally apparent that rotation of the shuttle during the operations described below is induced by either additional rotational drive coils, also disposed upon the cylinder, or alternatively, cooperating sets of permanent magnets disposed upon the shuttle and the end caps of the cylinder. In either event, it will be understood in the descriptions which follow that such systems are operating and their functions will be assumed to take place in the manner described below.

Returning to FIGS. 2A through 2C and FIGS. 3A through 3C, and with concurrent reference thereto, ventricular assist device 10 includes a cylinder 24 defining a cylinder bore 25 therethrough. Cylinder 24 further defines closed ends 34 and 35. Cylinder 24 also supports an input coupler 14 and an output coupler 15 both of which communicate with the interior of cylinder bore 25. A shuttle 26 is generally cylindrical and is precisely fitted within cylinder bore 25 so as to be freely movable therein. Shuttle 26 further defines a face 36 and a face 37. A cylinder head 28 comprises a volume within cylinder bore 25 confined by closed end 34 and face 36 of shuttle 26 together with a portion of cylinder bore 25 therebetween. Shuttle 26 also defines a blood flow channel 27 which is open at face 36 and closed at face 37.

Figure 4B:
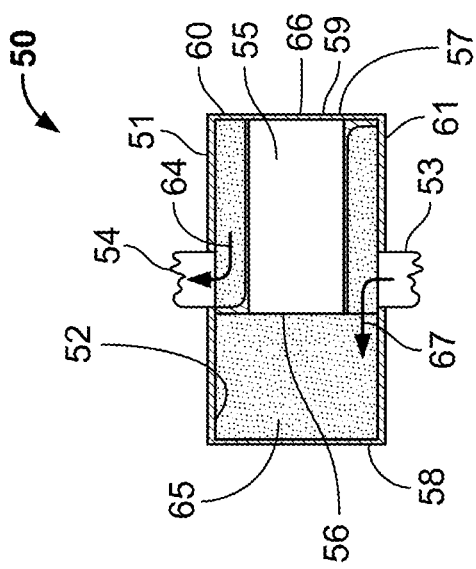
FIGS. 4A, 4B, 4C, 5A, 5B, and 5C taken together are sequential section views of an exemplary double acting ventricular assist device illustrating a complete operative cycle thereof.
Figure 4C:
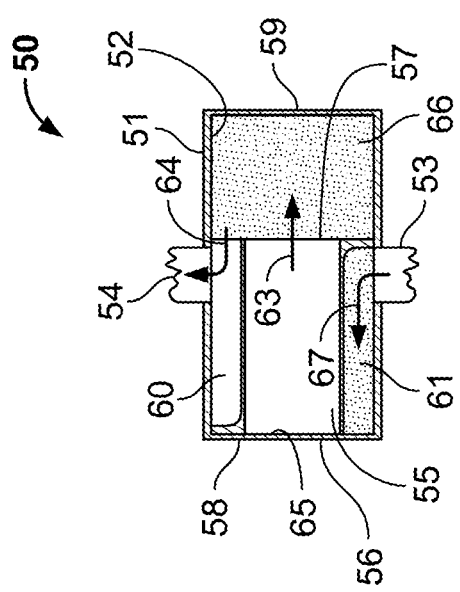
Figure 5B:
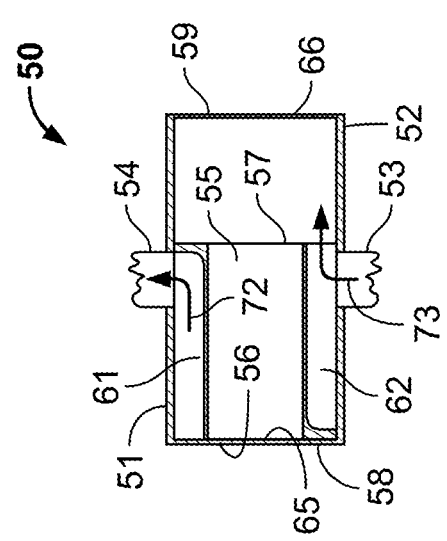
Figure 5C:
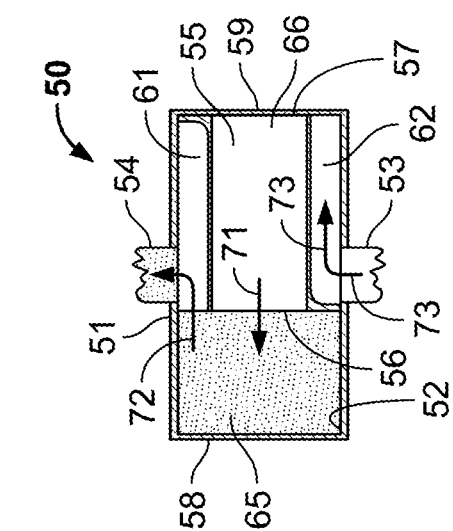
Figure 5A:
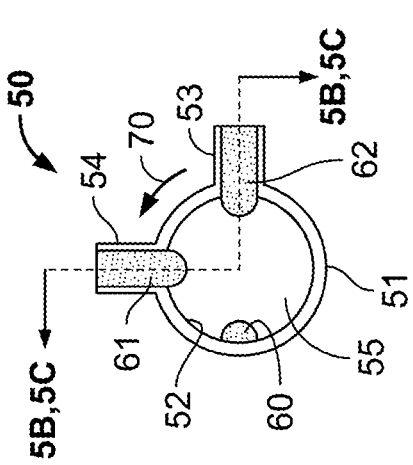
Figure 6:
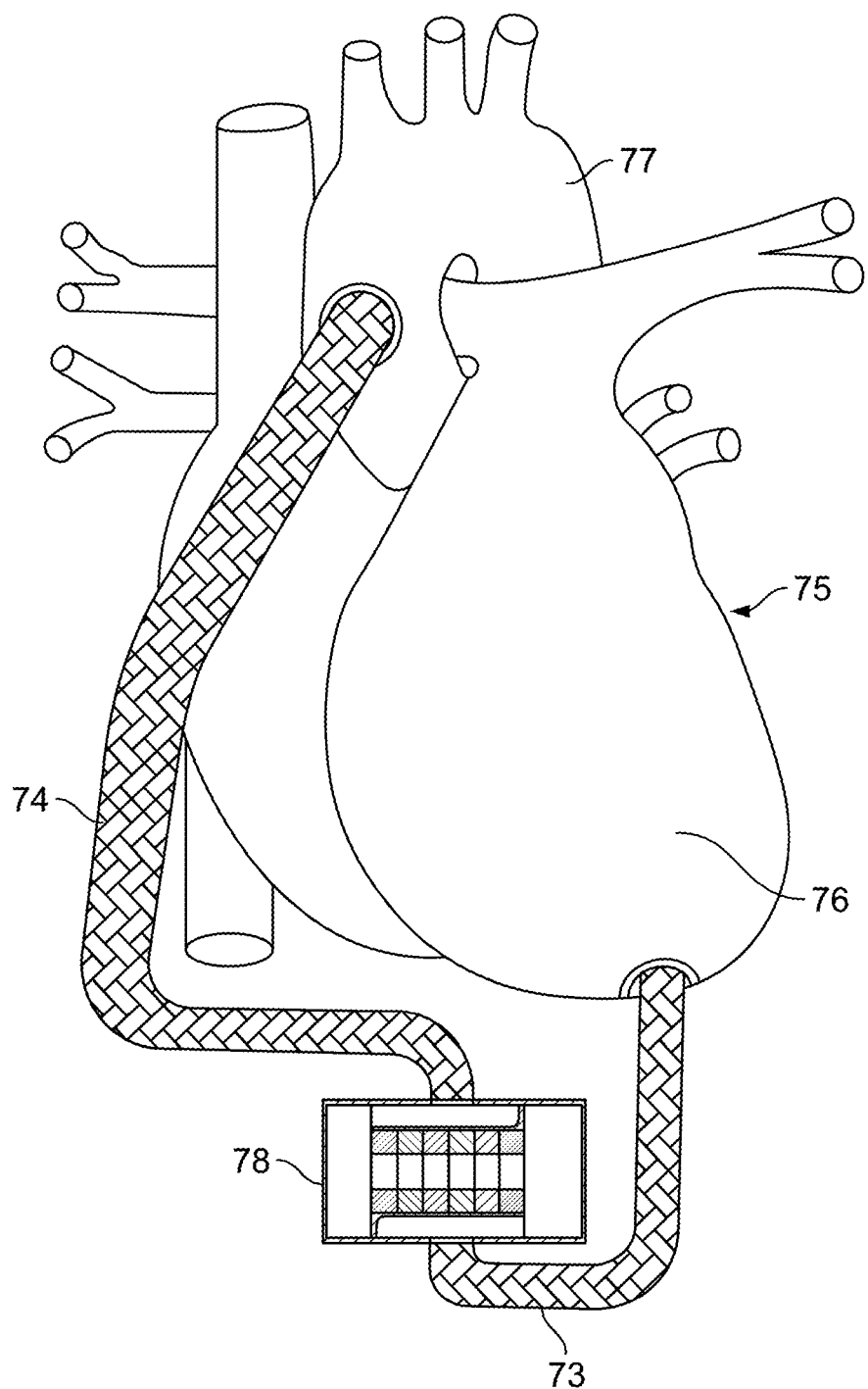
FIG. 6 is a connection diagram of an exemplary ventricular assist device utilized as a left ventricular assist device (LVAD) applied to a typical human heart.

FIG. 6 sets forth a connection diagram of the ventricular assist device utilized as a left ventricular assist device (LVAD) generally referenced by numeral 78 applied to a typical human heart generally referenced by numeral 75. Heart 75 is representative of a typical human heart and as such includes a left ventricle 76 and an aorta 77. In accordance with the customary connection of a left ventricle assist device application, ventricular assist device 78 is coupled to the lower end of left ventricle 76 by a flexible braided hose 73. In further accordance with conventional use, ventricular assist device 78 is coupled to aorta 77 by a flexible braided hose 74. In this application, ventricular assist device 78 may comprise ventricular assist device 10 shown in FIG. 1 or alternatively may comprise ventricular assist device 50 set forth and described above in FIGS. 4A through 5C. In either event, the basic ventricular assist is provided as ventricular assist de vice 78 flows blood from the lower end of left ventricle 76 which is pumped at increased pressure and strength through braided hose 74 into aorta 77 to supplement the presumably weakened performance of left ventricle 76. While not seen in FIG. 6, it will be understood that left ventricle assist device 78 is coupled to a source of operative control and power in the manner described above. This apparatus may alternatively be implanted within the patient or external to the patient in which case connection is made by a plurality of connecting wires (seen in FIG. 1).

Artificial Heart Devices

The artificial heart devices described herein may generally include a cylindrical housing comprising an exterior, first and second inlet ports, first and second outlet ports, a first end, and a second end, where the first and second ends defining a chamber therebetween. A shuttle may be contained within the chamber, where the shuttle may comprise an outer sleeve defining a hollow interior containing a plurality of magnets therein, and one or more channels longitudinally extending along the outer sleeve. The artificial heart may further include a magnetic actuation system operable to effect linear and rotational motion to the shuttle, where the linear motion of the shuttle pumps blood into and out of the chamber according to a pumping cycle, and the rotational motion of the shuttle selectively directs the flow of blood through the first and second inlet ports and the first and second outlet ports. The devices may also include a manifold associated with the cylindrical housing, the manifold comprising a first and second inlet, and a first and second outlet, wherein the first and second inlets and the first and second outlets are in fluid communication with corresponding ports of the first and second inlet ports and the first and second outlet ports.

Figure 7:
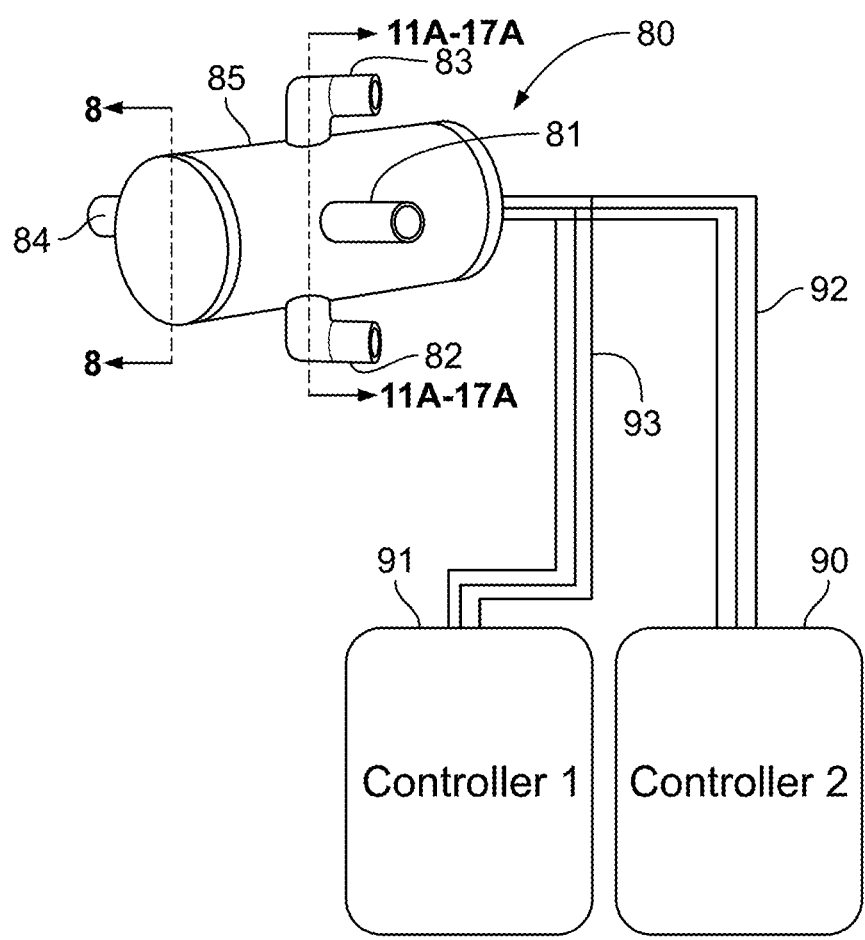
FIG. 7 is a perspective view of an exemplary double acting artificial heart embodiment coupled to a redundant pair of controllers.

FIG. 7 sets forth a perspective view of a double acting artificial heart 80, coupled to a redundant pair of controllers 90 and 91. Artificial heart 80 may be coupled to controllers 90 and 91 by a pair of cables 92 and 93 respectively. As mentioned above for the ventricular assist device, the coupling of artificial heart 80 via cables 92 and 93 will be similarly understood to be representative of either implanted installation of controllers 90 and 91 or, alternatively, external controllers 90 and 91. In the event the controllers are external to the patient, connections to artificial heart 80 implanted within the patient may be provided by cables 92 and 93 passing through the patient's skin. Artificial heart 80 may generally be cylindrical in shape and may optionally comprise an outer coating or layer of a biocompatible material 85. In the one variation of the artificial heart comprising a biocompatible coating or layer, the coating or layer 85 may be molded upon artificial heart 80 to completely seal and protect the artificial heart apparatus. A pair of inlets or input couplers 81 and 82 are supported upon artificial heart 80 and are spaced by a 90° angular spacing. A pair of outlets or output couplers 83 and 84 are similarly supported upon artificial heart 80 and are also spaced by a 90° angular spacing. The 90° angular spacing between inlets and the outlets is provided in order to be compatible with the 90° angular rotational increments applied to the shuttle in the manner described below in greater detail.

Figure 8:
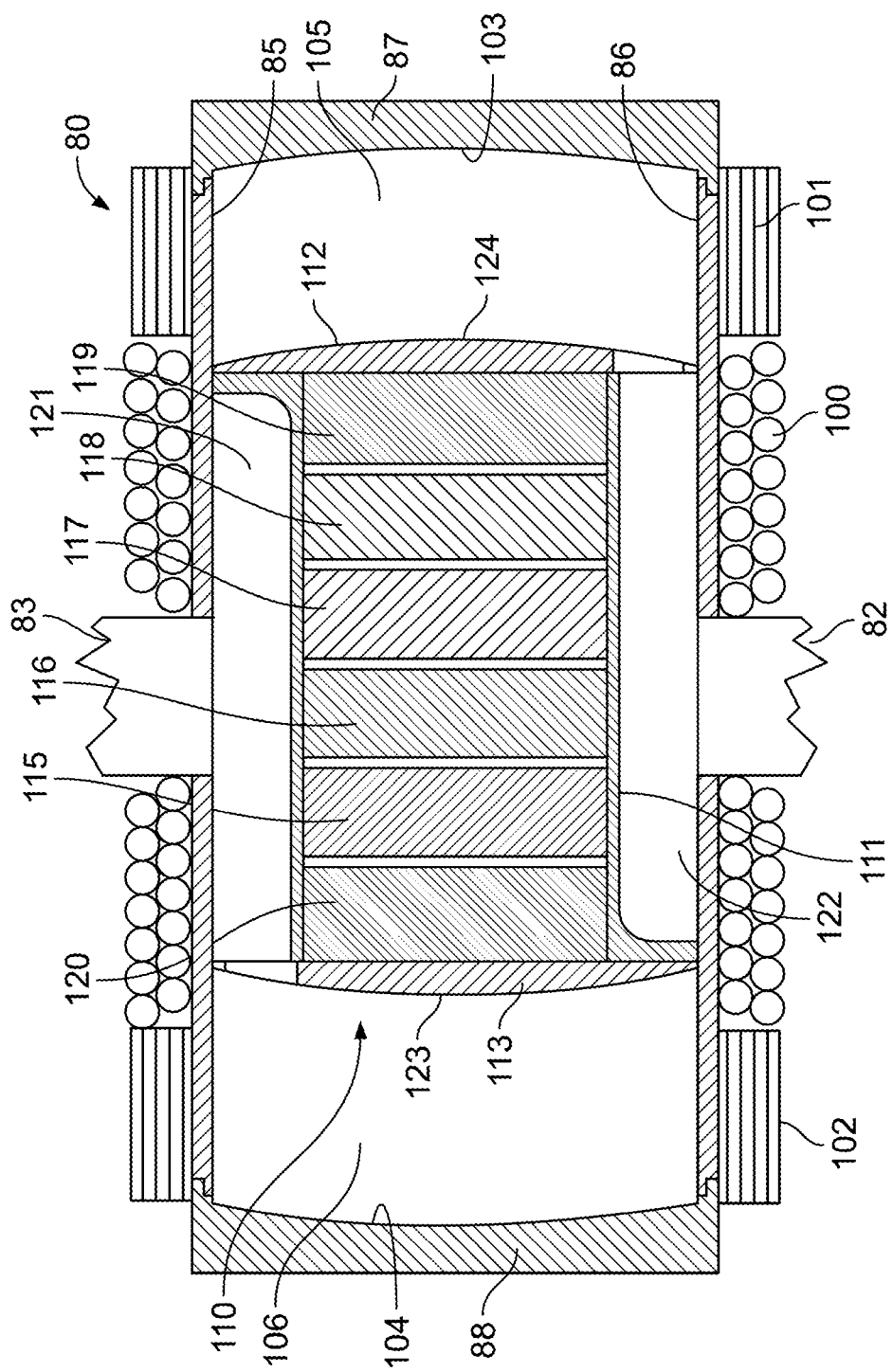
FIG. 8 is a section view of the artificial heart set forth in FIG. 7 taken along section lines 8-8 therein.

FIG. 8 sets forth a section view of artificial heart 80 as set forth above in FIG. 7 taken along section lines 8-8 therein. Artificial heart 80 includes a shuttle 110 which is movable within a cylinder 85. Cylinder 85 defines a cylinder bore 86 having a pair of end caps 87 and 88 joined at opposite ends thereof. The combination of cylinder 85 and end caps 87 and 88 form a closed end cylinder within which shuttle 110 is freely movable and precisely fitted. Shuttle 110 includes a magnet supporting sleeve 111 which defines a pair of blood flow channels 121 and 122. Shuttle 110 further includes a plurality of linear motion magnets 115, 116, 117 and 118 supported within magnet support sleeve 111 and secured by mutual magnetic attraction and, in some instances, a conventional adhesive or other attachment. Shuttle 110 further supports a rotational motion magnet 119 at one end adjacent linear motion magnet 118 together with a rotational motion magnet 120 adjacent linear motion magnet 115 at the opposite end. The structure of shuttle 110 is completed by an end cap 112 secured to magnet supporting sleeve 111 adjacent rotational motion magnet 119 together with an end cap 113 secured to magnet supporting sleeve 111 adjacent rotational motion magnet 120. End caps 112 and 113 are joined to magnet support sleeve 111 and magnets 119 and 120 using a conventional biocompatible adhesive or similar attachment.

Artificial heart 80 further includes an input 82 and an output 83 both of which extend into cylinder bore 86. A plurality of linear motion coils 100 are wound upon the outer surface of cylinder 85. A plurality of rotational motion coils 101 are wound upon one end of cylinder 85 while a second plurality of rotational motion coils 102 are wound upon the opposite end of cylinder 85. Linear motion coils 101 and rotational motion coils 101 and 102 are each coupled to a controller (seen in FIG. 7) which provide appropriate electrical signals for driving artificial heart 80. As mentioned above, artificial heart 80 is coated with an outer molded encapsulation (seen in FIG. 1) which seals and protects the components within artificial heart 80.

In operation, a reciprocating linear motion is imparted to shuttle 110 within cylinder bore 86 by energizing linear motion coils 100. Similarly, rotational motion is imparted to shuttle 110 by energizing rotational motion coils 101 and 102 at each end of the travel of shuttle 110. A cylinder head volume 106 is defined between face 104 of end cap 88 and face 123 of end cap 113 together with a portion of cylinder bore 86 therebetween. Thus, the volume of cylinder head 106 is determined by the linear position of shuttle 110 within cylinder bore 86. In accordance with one aspect, the curvature of face 104 defines a greater radius of curvature than that of face 123. As a result, shuttle 110 is able to be driven against face 104 without conforming to face 104 thereby avoiding the creation of a vacuum attachment therebetween which would otherwise impede the movement of shuttle 110 away from face 104.

Similarly, a cylinder head volume 105 is defined between face 104 of end cap 87 and face 124 of end cap 112 together with a portion of cylinder bore 86 therebetween. Thus, the volume of cylinder head 105 is determined by the linear position of shuttle 110 within cylinder bore 86. Once again, the curvature of face 103 defines a greater radius of curvature than that of face 124. As a result, shuttle 110 is able to be driven against face 104 without conforming to face 104 thereby avoiding a vacuum attachment therebetween which would otherwise impede the movement of shuttle 110 away from face 103.

Figure 9:
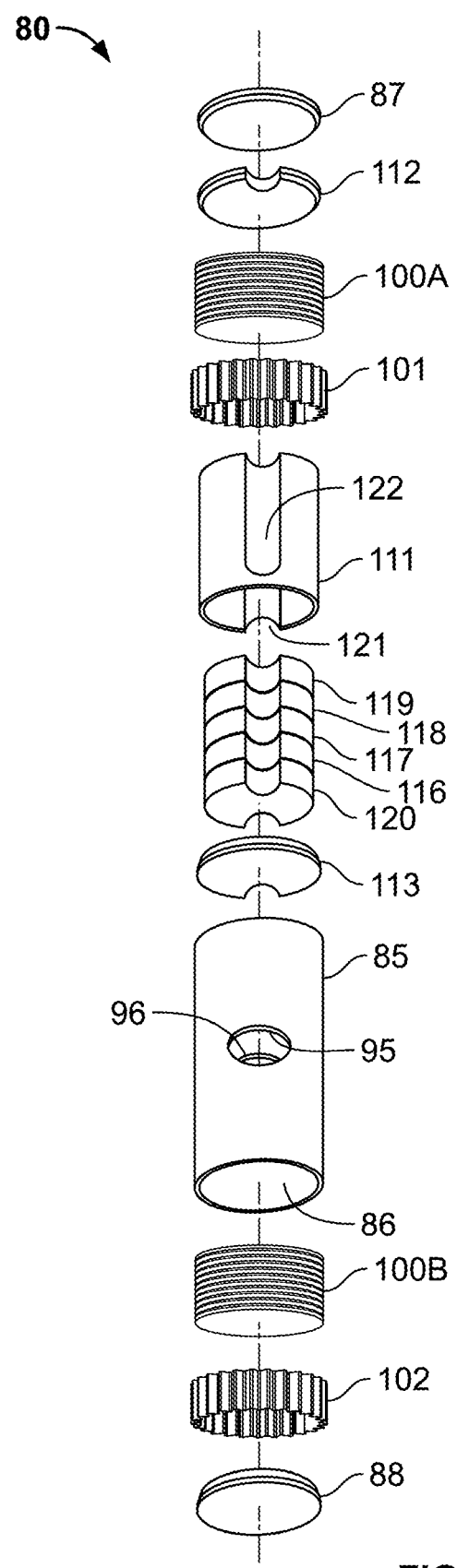
FIG. 9 is a perspective assembly view of an alternate embodiment of an artificial heart utilizing rotational coils for rotational shuttle movement and linear coils for linear movement.

FIG. 9 sets forth a perspective assembly view of artificial heart 80. Artificial heart 80 includes a shuttle 110 (seen in FIG. 8) which is fabricated of a plurality of linear motion magnets 116, 117 and 118 together with a pair of rotational motion magnets 119 and 120 joined together to form a magnet stack. A sleeve 111 defining a pair of blood flow channels 121 and 122 receives magnets 116 through 120. A pair of end caps 112 and 113 are fitted to magnet support sleeve 111 to complete shuttle 110 (seen in FIG. 8).

Artificial heart 80 further includes a cylinder 85 defining a cylinder bore 86 therethrough. Shuttle 110 is received within cylinder bore 86 after which end caps 87 and 88 are secured to the ends of cylinder 85 to complete the closed end structure thereof and captivate shuttle 110 (seen in FIG. 8). Cylinder 85 further defines apertures 95 and 96 which receive output 83 and input 82 (seen in FIG. 8). While not seen in FIG. 9, it will be noted by temporary reference to FIG. 7 that artificial heart 80 further includes an input 81 and an output 84. Thus, it will be understood that cylinder 85 further defines a pair of apertures similar to apertures 95 and 96 on each side thereof which accommodate input 81 and output 84. Returning to FIG. 9, linear motion coils 100A and 100B combine to form linear motion coils 100 which are supported on either side of apertures 95 and 96. Rotational motion coils 101 and 102 are fitted upon the ends of cylinder 85. Once the assembly of artificial heart 80 is complete, an outer protective covering of a biocompatible material (not shown) is formed upon the entire outer surface of artificial heart 80 in a process such as injection molding or the like.

In some aspects of the described devices, a tight tolerance or precision fit is provided between the shuttle and the cylinder bore, which minimizes the clearance gap between the shuttle and the cylinder bore. The shuttle remains freely movable both laterally and rotationally within the cylinder bore and the shuttle and the cylinder bore remain free of any utilization of additional sealing apparatus such as O-rings, gaskets, resilient seals, diaphragms or the like. Instead, the above described devices fabricate the cylinder and the magnet support sleeve of the shuttle from a ceramic material such as synthetic sapphire or zirconia. In addition, the precision machining of both the cylinder bore and the magnetic support sleeve is extremely precise such that the clearance between the outer surface of the magnet support sleeve and the interior surface of the cylinder bore is maintained between two to three microns (2.0-3.0 µm). This clearance gap is smaller than the typical size of blood cells. Thus, as blood is pumped within the ventricular assist devices and artificial hearts, blood cells do not migrate between the outer surface of the magnet support sleeve and the inner surface of the cylinder bore.

Returning to FIG. 9 specifically, and in view of the above descriptions of the precision fit between the shuttle exterior surface and the cylinder bore, it will be understood that once shuttle 110 (seen in FIG. 8) has been fully assembled and the outer surface of magnet support sleeve 111 has been precisely machined, cylinder bore 86 of cylinder 85 is also precisely machined such that the above described 2.0 to 3.0 micron clearance exists between magnet support sleeve 111 and cylinder bore 86. Once shuttle 110 (seen in FIG. 8) has been received within cylinder bore 86, end caps 87 and 88 are secured to the ends of cylinder 85. Thereafter, the above described outputs and inputs are joined to cylinder 85 and finally, linear motion coils 100A and 100B together with rotational motion coils 101 and 102 are positioned upon the exterior surface of cylinder 85 and appropriate electrical connections (not shown) are made. The assembly is completed as the above described outer coating of biocompatible material is molded upon, or otherwise placed upon, the exterior of artificial heart 80 to seal the entire structure.

In operation, artificial heart 80 is operative to move shuttle 110 (seen in FIG. 8) in a linear motion within cylinder bore 86 under the influence of linear motion coils 100A and 100B as they interact with linear motion magnets 115 through 118. Similarly, shuttle 110 undergoes rotational motion at each end of its linear travel in the manner described below by virtue of the interaction of each of the rotational magnets supported at each end of shuttle 110. Thus, as shuttle 110 approaches end 87, rotational magnet 119 supported upon shuttle 110 interacts with rotational motion coil 101 to provide the rotational movement of shuttle 110 described below in greater detail. Similarly, as shuttle 110 approaches end cap 88 within cylinder bore 86, rotational magnet 120 interacts with rotational motion coil 102 to induce rotational movement of shuttle 110 described below. The operative motions of linear travel and rotational movement that comprise an operative cycle of both artificial heart 130 (seen in FIG. 10) and artificial heart 80 are set forth below in greater detail in FIGS. 11A through 17C.

Figure 10:
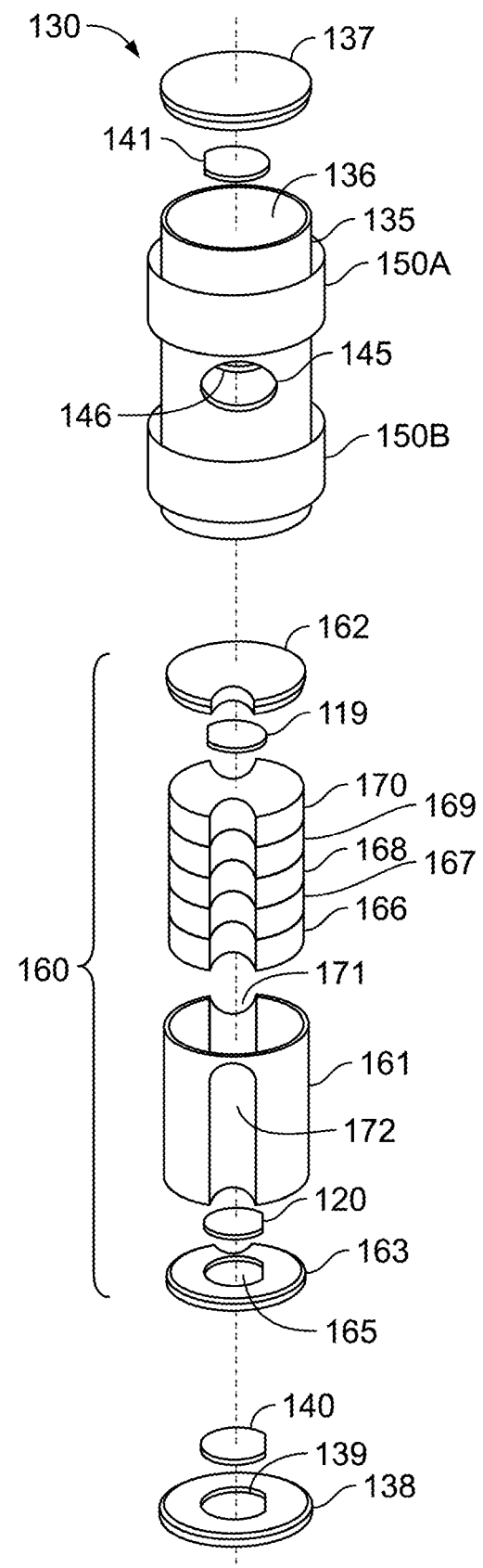
FIG. 10 is a perspective assembly view of an artificial heart utilizing permanent magnets for rotational shuttle movement.

FIG. 10 sets forth a perspective assembly view of an alternate embodiment of the artificial heart generally referenced by numeral 130. Artificial heart 130 is substantially similar to artificial heart 80 with the difference being found in the utilization within artificial heart 130 of cooperating pairs of permanent magnets to provide rotation of shuttle 160 rather than the combination of rotational motion coils and cooperating magnets utilized in artificial heart 80. In all other respects however the function and operation of artificial heart 130 is substantially the same as artificial heart 80. Artificial heart 130 includes a shuttle 160 which is fabricated of a plurality of linear motion magnets 166, 167, 168, 169 and 170 joined together to form a magnet stack. Shuttle 160 further includes a pair of rotational motion magnets 119 and 120 supported within end caps 162 and 163 respectively. A magnet support sleeve 161 defining a pair of blood flow channels 171 and 172 receives magnets 166 through 170. End caps 162 and 163 are fitted to magnet support sleeve 161 to complete shuttle 160. Rotational magnet 120 is received within a recess 165 formed on the interior of end cap 163. While not seen in FIG. 10, it will be understood that end cap 162 is identical to end cap 163 and thus defines a similar recess to recess 165 which receives rotational magnet 119.

Artificial heart 130 further includes a cylinder 135 defining a cylinder bore 136 therethrough. Shuttle 160 is received within cylinder bore 136 after which end caps 137 and 138 are secured to the ends of cylinder 135 to complete the closed end structure thereof and captivate shuttle 160. Cylinder 135 further defines apertures or ports 145 and 146 which receive outlets and inlets of a manifold (not shown). While also not seen in FIG. 10, it will be noted by temporary reference to FIG. 7 that artificial heart 80 further includes an additional input and an additional output. Thus, it will be understood that cylinder 135 further defines a pair of apertures similar to apertures 145 and 146 on each side thereof which accommodate an additional input and output. Linear motion coils 150A and 150B combine to form linear motion coils 150 which are supported on either side of apertures 145 and 146. End caps 137 and 138 are joined to the ends of cylinder 135 to captivate shuttle 160 within cylinder bore 136. It will be noted that end cap 138 defines a recess 139 which receives a rotational magnet 140. While not seen in FIG. 10, it will be understood that end cap 137 is identical to end cap 138 and thus defines a magnet receiving recess identical to recess 139. Accordingly, rotational magnet 141 will be understood to be received within and supported within end 137. Once the assembly of artificial heart 130 is complete, an outer protective covering of a biocompatible material (not shown) is formed upon the entire outer surface of artificial heart 130 in a process such as injection molding or the like.

In operation, artificial heart 130 is operative to move shuttle 160 in a linear motion within cylinder bore 136 under the influence of linear motion coils 150A and 150B as they interact with linear motion magnets 166 through 170. Similarly, shuttle 160 undergoes rotational motion at each end of its linear travel in the manner described below by virtue of the interaction of each of the pairs of rotational magnets supported at each end of artificial heart 130. Thus, as shuttle 160 approaches end 137, rotational magnet 119 supported upon shuttle 160 within end cap 162 interacts with rotational magnet 141 supported within end cap 137 to provide the rotational movement of shuttle 160 described below in greater detail. Similarly, as shuttle 160 approaches end cap 138 within cylinder bore 136, rotational magnet 140 within end cap 138 interacts with rotational magnet 120 supported upon shuttle 160 within end cap 165 interacts to induce rotational movement of shuttle 160 described below. The operative motions of linear travel and rotational movement that comprise an operative cycle of both artificial heart 80 (seen in FIG. 9) and artificial heart 130 are set forth below in greater detail in FIG. 11A through 17C.

FIG. 11A sets forth a section view of artificial heart 80 taken along section lines 11A, 17A-11A, 17A in FIG. 7. FIG. 11B sets forth a section view of artificial heart 80 taken along section lines 11B-11B in FIG. 11A. FIG. 11C sets forth a section view of artificial heart 80 taken along section lines 11C-11C in FIG. 11A. FIG. 11A sets forth an end view of artificial heart 80 which facilitates the illustration of the rotational position of shuttle 110 and blood flow channels 121 and 122 formed therein relative to inputs 81 and 82 as well as outputs 83 and 84 of artificial heart 80. The section view of FIG. 11B facilitates the illustration of the action within artificial heart 80 as shuttle 110 is moved within cylinder bore 86 in relation to input 82 and the output 83. Finally, the section view of FIG. 11C facilitates the illustration of the action within artificial heart 80 as shuttle 110 is moved within cylinder bore 86 relative to input 81 and output 84. When taken together, FIGS. 11A, 11B and 11C illustrate the operation of artificial heart 80 at a specific point during its operational cycle. In a similar fashion, FIGS. 12A through 12C, 13A through 13C, 14A through 14C, 15A through 15C, 16A through 16C and 17A through 17C provide illustrations of other points within the operational cycle of artificial heart 80.

While it will be understood that the operation of artificial heart 80 is a continuous operation in which the operational cycle described below is continuously repeated, it is believed that the operation of artificial heart 80 may be more readily understood by examining a sequence of selected points within the operational cycle. The selected points within the operational cycle as well as the selected starting point and finishing point for these explanations which follow is purely arbitrary and chosen as a matter of convenience.

Thus, with concurrent reference to FIGS. 11A, 11B and 11C artificial heart 80 is shown in simplified depiction in which artificial heart 80 includes a cylinder 85 within which a shuttle 110 is captivated. Shuttle 110 defines blood flow channels 121 and 122. Cylinder 85 supports inputs 81 and 82 together with outputs 83 and 84. At the point of the operational cycle depicted in FIGS. 11A through 11C, shuttle 110 is rotated to align blood flow channel 121 with input 82 and blood flow channel 122 with output 83. At this point of operation, shuttle 110 has just completed a linear movement to the right and is positioned against end 126 of cylinder 85. In the movement to the right ending in this position, the alignment of blood flow channel 121 with input 82 during this movement has caused a blood flow into cylinder head volume 127 which completely fills cylinder head 127. Concurrently, the movement to the right by shuttle 110 has also fully displaced the blood volume within cylinder head 128 and thus cylinder head 128 defines a minimum volume. This defines a selected start point or illustration of an operational cycle of artificial heart 80. Once again it will be understood that this starting point is selected as a matter of convenience and the operation of artificial heart 80 is substantially continuous.

Figure 12C:
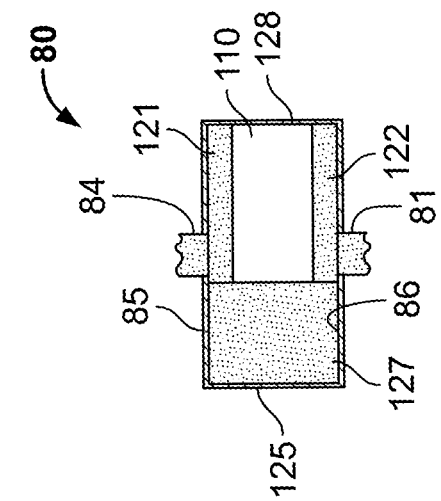
Figure 12B:
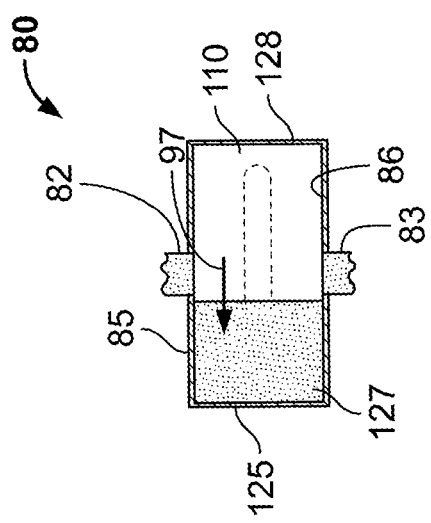
Figure 12A:
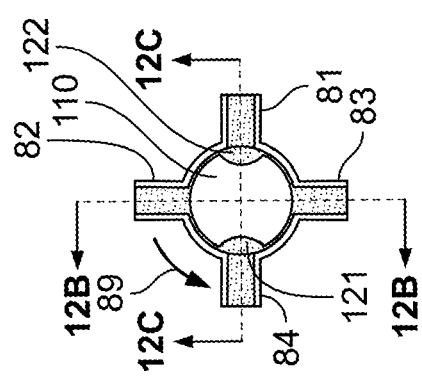

The next operational cycle is initiated as shuttle 110 is rotated in a counterclockwise direction indicated by arrow 89 causing artificial heart 80 to assume the position shown in FIGS. 12A through 12C. It is important to note that the rotation of shuttle 110 has aligned blood flow channels 121 and 122 with output 84 and input 81 respectively. It is also important to note that this rotational position of shuttle 110 has closed input 82 and output 83 (best seen in FIG. 13B). Once shuttle 110 has been rotated, linear movement of shuttle 110 in the left direction indicated by arrow 97 is initiated by activating the linear motion coils of artificial heart 80 (seen in FIG. 9) causing shuttle 110 to move to the left and assume the position shown in FIGS. 13A through 13C.

FIGS. 13A through 13C illustrate the position of artificial heart 80 as shuttle 110 moves to the left. Shuttle 110 continues to be rotationally positioned such that blood flow channels 121 and 122 are aligned with output 84 and input 81 respectively and such that input 82 and output 83 are closed. With particular attention to FIG. 13C, the movement of shuttle 110 in the direction indicated by arrow 97 displaces the blood volume within cylinder head 127 causing it to flow outwardly through blood flow channel 121 and output 84 in the direction indicated by arrow 98. Simultaneously, the movement to the left in the direction indicated by arrow 97 of shuttle 110 also increases the volume of cylinder head 128. This increased volume, in turn, draws blood in through input 81 and blood flow channel 122 filling cylinder head 128. This simultaneous displacement of blood volume from cylinder head 127 and replenishment of the other blood volume within cylinder head 128 is a consequence of the double acting character of the pumping action of artificial heart 80. The movement to the left of shuttle 110 continues until shuttle 110 reaches end 125 of cylinder 85 at which point artificial heart 80 assumes the position shown in FIGS. 14A through 14C.

FIGS. 14A through 14C illustrate the point in the operative cycle of artificial heart 80 when shuttle 110 has reached its farthest left position against end 127 of cylinder 85. At this point, cylinder head 127 is at its minimum volume while cylinder head 128 holds a maximum blood volume. The operational cycle of artificial heart 80 continues as shuttle 110 is rotated. Clockwise in the direction indicated by arrow 109 to the position shown in FIGS. 15A through 15C.

Figure 15C:
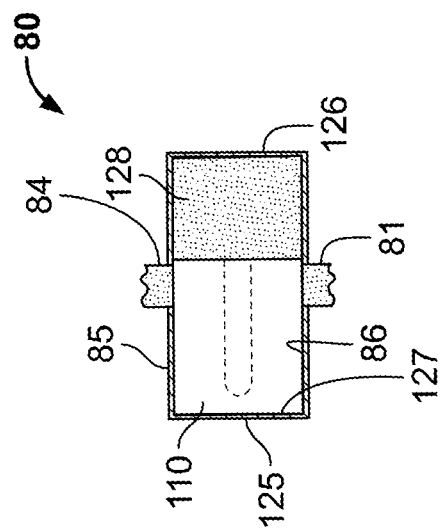
Figure 15B:
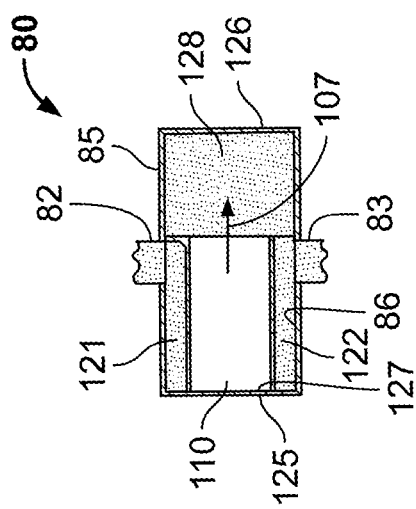
Figure 15A:
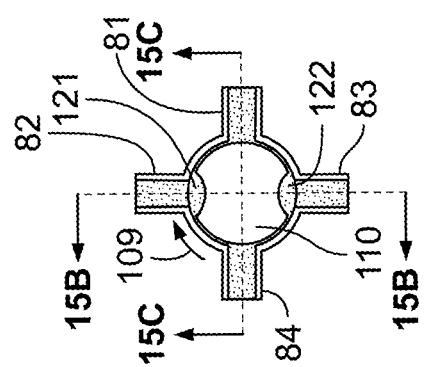

FIGS. 15A through 15C show the point in the operational cycle of artificial heart 80 at which shuttle 110 has reached its maximum left position and has been rotated in the direction indicated by arrow 109 to the position shown in FIG. 15A. It is important to note that the rotational position of shuttle 110 now aligns blood flow channels 121 and 122 with input 82 and output 83 respectively while input 81 and output 84 are closed. The operational cycle of artificial heart 80 continues as the linear motion coils (seen in FIG. 9) are again energized causing shuttle 110 to be moved to the right in the direction indicated by arrow 107. As shuttle 110 moves in the direction indicated by arrow 107, artificial heart 80 moves to the position shown in FIGS. 16A through 16C.

FIGS. 16A through 16C set forth the operational cycle of artificial heart 80 as shuttle 110 continues to move in the direction indicated by arrow 107. With blood flow channel 121 aligned with input 82 this movement increases the volume of cylinder head 127 drawing blood through input 82 and blood flow channel 121 in the direction indicated by arrow 132 filling cylinder head 127. Simultaneously, this movement of shuttle 110 and the alignment of blood flow channel 122 during this movement displaces the blood volume within cylinder head 128 causing blood to flow outwardly through blood flow channel 122 and output 83 in the direction indicated by arrow 131. It will be noted that, as is best seen in FIG. 16C, the rotational position of shuttle 110 maintains input 81 and output 84 closed. The blood flow in the direction of arrows 132 and 131 continues as shuttle 110 continues moving in the direction indicated by arrow 107 until shuttle 110 reaches end 126 of cylinder 85 and artificial heart 80 assumes the position shown in FIGS. 17A through 17C.

FIGS. 17A through 17C set forth the end point of the described operational cycle of artificial heart 80 as shuttle 110 reaches its farthest right position. At this position, cylinder head 127 holds a maximum blood volume while cylinder head 128 holds a minimum blood volume. It will be recognized that the position of artificial heart 80 shown in FIGS. 17A through 17C corresponds to that shown in FIGS. 11A through 11C. Thus, artificial heart 80 has completed an operational cycle and returned to the selected starting point utilized in the foregoing descriptions and illustrations. The operation of artificial heart 80 continues as the above-described sequence is repeated.

It will be understood that the foregoing operation described for artificial heart 80 is the same operation as the operation formed by artificial heart 130. Accordingly, the descriptions and illustrations set forth above for artificial heart 80 will be understood to apply with equal force to artificial heart 130.

Figure 18:
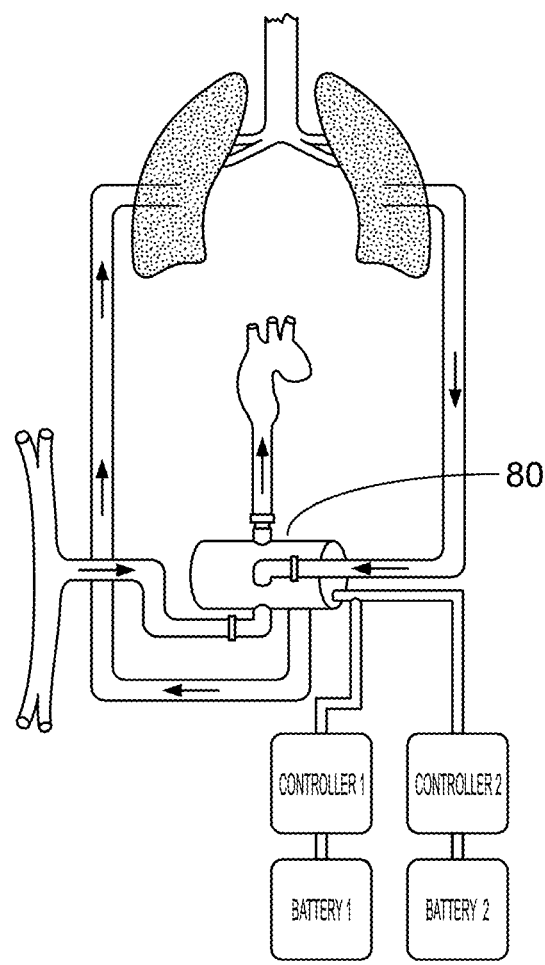
FIG. 18 illustrates an application of an exemplary artificial heart to an illustrative representation of a human circulatory system.

FIG. 18 sets forth a functional diagram illustrating artificial heart 80 positioned in association with an illustrative human heart and lung depiction. It will be understood that FIG. 18 is merely representative of this cooperation and is not a detailed representation of the individual couplings utilized when artificial heart 80 is implanted. In addition, it will be further understood that the illustration shown in FIG. 18 is equally representative of the use of artificial heart 130.

Figure 19:
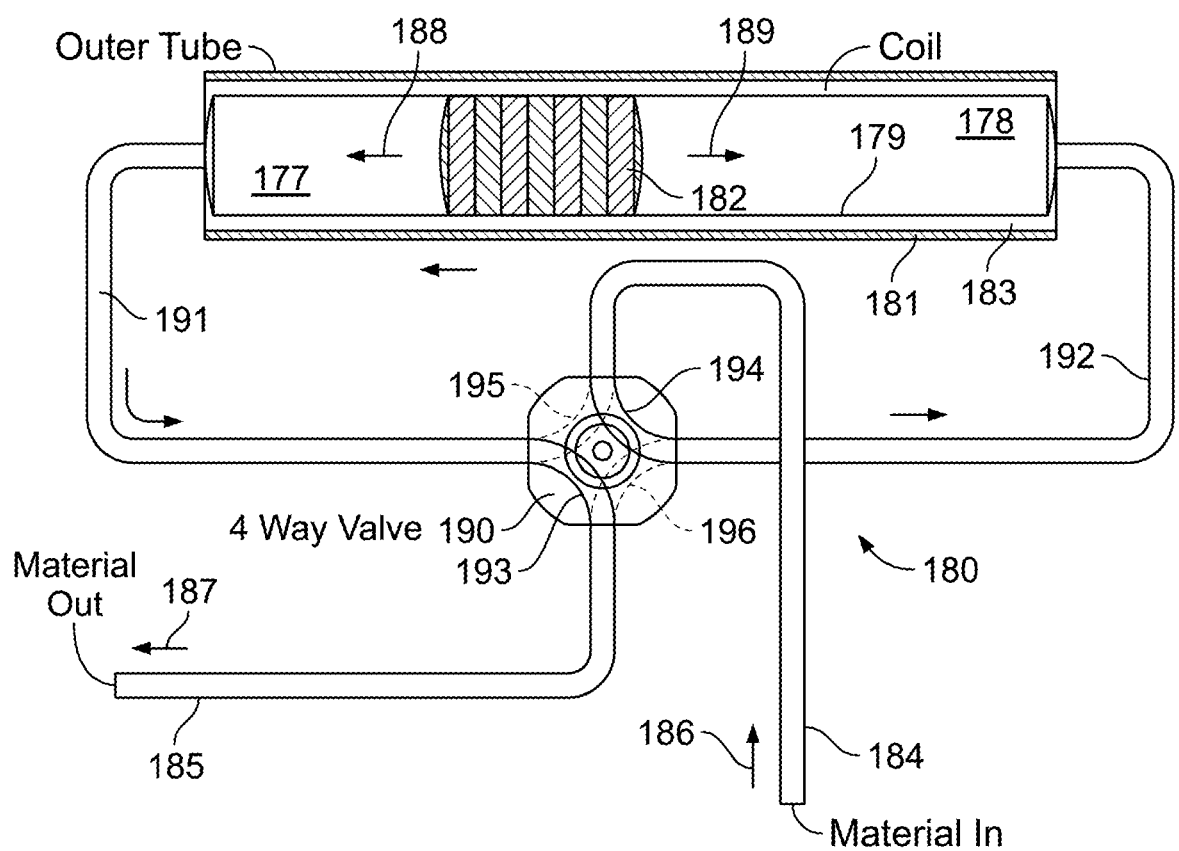
FIG. 19 is a variation of a pump device that utilizes an externally operative four-way valve.

FIG. 19 sets forth a further alternate embodiment generally referenced by numeral 180 in which an external valve is utilized to provide the flow reversal required to accommodate the reciprocating motion of the shuttle within the pump. Pump 180 utilizes a cylinder 181 having a set of linear motor coils 183 wound upon the exterior there. Within a bore 179, a shuttle 182 supporting a plurality of permanent magnets is linearly movable in the directions indicated by arrows 188 and 189. A pair of coupling tubes 191 and 192 extend from opposed ends of cylinder 181 and are connected to a four-way valve 190. Four-way valve 190 includes a pair of coupling passages 193 and 194 which may be positioned as shown in solid line representation or alternatively may be switched to an alternate position as shown by dashed line connections 195 and 196. The output of four-way valve 190 is connected to an output 185 which is intended to flow material in the direction indicated by arrow 187. The input of four-way valve 190 is connected to an input tube 184 which is intended to flow material in the direction indicated by arrow 186.

In operation, with four-way valve 190 positioned in accordance with the solid line couplings 193 and 194 shown, linear motor coils 183 are energized to drive shuttle 182 in the direction indicated by arrow 188. This motion of shuttle 182 displaces material within volume 177 causing material to flow outwardly from cylinder 181 to four-way valve 190 through passage 193 and outwardly in the direction indicated by arrow 187 through coupling 185. Simultaneously, the movement of shuttle 182 in the direction indicated by arrow 188 draws material inwardly into the confined volume within volume 178. This flow draws material through input 192 and coupling 194 of four-way valve 190. This in turn draws material through connecting tube 184 in the direction indicated by arrow 86.

When shuttle 182 reaches its end of travel in the direction indicated by arrow 188, the excitation of coils 183 is reversed driving shuttle 182 in the direction indicated by arrow 189. At the same time, four-way valve 190 is switched to the positions shown as dashed line couplings 195 and 196. As shuttle 182 travels in the direction indicated by arrow 189 it displaces the material volume within volume 178 driving it outwardly through coupling 192. The flow of material through coupling 182 is transferred to output 185 by dashed line four-way valve coupling 196 causing an outward flow in the direction indicated by arrow 187. In addition, the movement of shuttle 182 in the direction indicated by arrow 189 draws material into volume 177 through coupling 191. Dashed line coupling 195 of four-way valve 190 connects coupling 191 to input 184 causing material to be drawn in the direction indicated by arrow 186. This action continues as shuttle 182 is reciprocated within cylinder bore 179 and four-way valve 190 is switched in synchronized fashion therewith.

Methods

Pumping Blood Using a Ventricular Assist Device

Methods of pumping blood in a recipient are also described herein. The methods generally include linearly reciprocating a shuttle contained within a housing to simultaneously move blood into and out of the housing, the housing comprising a plurality of ports, and rotating the shuttle to selectively direct the movement of blood into and out of the plurality of ports. The shuttle generally reciprocates according to a pumping cycle that may be preset by a physician and then adjusted based on feedback on one or more detected parameters of the recipient. Such parameters may include signs such as heart rate or blood pressure, or symptoms such as shortness of breath or lightheadedness. The housing may be implanted within the recipient or reside outside the recipient with connections traversing through the skin to reach the appropriate vasculature and/or heart chamber.

When the housings are implanted, a first port of the plurality of ports may be coupled to the aorta of the recipient, and a second port of the plurality of ports may be coupled to the left ventricle of the recipient. This configuration of couplings may be useful when the devices are ventricular assist devices.

In one embodiment, the ventricular assist device works to either pump blood or fill with blood with each shuttle stroke or reciprocation (single-acting reciprocation). Here, a single channel of the shuttle may be aligned with the first port, which is an input port, resulting in blockage of the second port, which is an output port. Linear movement of the shuttle then moves blood from the left ventricle through the input port and into the housing. After the shuttle has completed its stroke, it is then rotated to align the channel with the output port, which closes the input port. Linear movement of the shuttle then moves blood from the housing through the output port and into the aorta, completing a pumping cycle. The cycle is then repeated to assist with blood circulation in the recipient.

For example, referring to FIGS. 2A-2C and FIGS. 3A-3C, ventricular assist device 10 is shown at the start of a pump cycle which is initiated as shuttle 26 is rotated to align channel 27 with input 14. As a result, output 15 is simultaneously blocked by this rotational position of shuttle 26.

Referring to FIG. 2B, shuttle 26 is shown at the initiation of a pump cycle in which shuttle 26 is at its left position in which face 36 of shuttle 26 is close to end 34 of cylinder 24. At this point, the volume of cylinder head 28 is at a minimum and is near zero. The pump stroke begins as shuttle 26 is driven to the right toward end 35 of cylinder 24 in the direction indicated by arrow 29. The movement of shuttle 26 in the direction indicated by arrow 29 increases the volume within cylinder head 28 which, in turn, draws blood from input 14 into channel 27 in the direction indicated by arrow 30. As the shuttle movement in the direction indicated by arrow 29 continues, the volume of cylinder head 28 is further increased drawing additional blood into cylinder head 28 and filling cylinder head 28 with blood until shuttle 26 reaches its extreme right position shown in FIG. 2C.

Furthermore, FIG. 2C shows ventricular assist device 10 at the point at which shuttle 26 has moved fully to the right and face 37 of shuttle 26 is against end 35 of cylinder 24. At this point, a maximum volume of blood is confined within cylinder head 28. Shuttle 26 is then rotated from the position shown in FIG. 2A to the position shown in FIG. 3A.

FIG. 3A sets forth a section view of ventricular assist device 10 taken along section lines 2A, 3A-2A, 3A in FIG. 1. FIG. 3A sets forth ventricular assist device 10 at the midpoint of a pump cycle at which shuttle 26 is rotated to align channel 27 with output 15. As a result, output 15 is aligned with channel 27 of shuttle 26 and input 14 is simultaneously blocked by this rotational position of shuttle 26.

FIG. 3B shows shuttle 26 at its right position in which face 36 of shuttle 26 is farthest from end 34 of cylinder 24. At this point, the volume of cylinder head 28 is at its maximum. The pump stroke continues as shuttle 26 is driven to the left toward end 34 of cylinder 24 in the direction indicated by arrow 32. The movement of shuttle 26 in the direction indicated by arrow 32 displaces the volume within cylinder head 28 which, in turn, drives blood into channel 27 and outwardly through output 15 in the direction indicated by arrow 33. As the shuttle movement in the direction indicated by arrow 32 continues, the volume of blood within cylinder head 28 is further displaced forcing additional blood from cylinder head 28 until shuttle 26 reaches its extreme left position shown in FIG. 3C.

FIG. 3C shows ventricular assist device 10 at the point at which shuttle 26 has moved fully to the left and face 36 of shuttle 26 is against end 34 of cylinder 24. At this point, the confined blood volume blood volume within cylinder head 28 has been displaced outwardly through output 15. Shuttle 26 is then rotated from the position shown in FIG. 3A back to the position shown in FIG. 2A at which point the pump cycle is complete and is repeated in the above scribed sequence.

The above-described sequence of operations may be carried forward on a repetitive basis as ventricular assist device 10 performs to provide a simple and easy to manufacture ventricular assist device utilizing a single acting pumping action. This pumping action may be carried forward as blood flow channel 27 is rotated into alignment with input 14 each time that shuttle 26 is moved to the right (arrow 29) and is rotated into alignment with output 15 each time that shuttle 26 is moved to the left (arrow 32). Cylinder head 28 is filled with a blood volume during each movement of shuttle 26 to the right which blood volume is then displaced through output 15 during each movement of shuttle 26 to the left.

In another embodiment, the ventricular assist device works to both pump blood and fill with blood with each shuttle stroke or reciprocation (double-acting reciprocation). In this embodiment, the shuttle includes three channels. The linear and rotational movement of the shuttle to align the channels with ports and allow fluid communication therethrough or to block the of blood into the chamber (cylinder heads 65 and 66) is described in detail by referring to FIGS. 4A to 4C and FIGS. 5A to 5C.

With temporary reference to FIGS. 8, 9 and 10, it will be seen that ventricular assist device 50 is also driven in a linear motion by a plurality of linear motor coils encircling the cylinder together with permanent magnets disposed within the interior of the shuttle. In addition, it will be equally apparent that rotation of the shuttle during the operations described below is induced by either additional rotational drive coils, also disposed upon the cylinder, or alternatively, cooperating sets of permanent magnets disposed upon the shuttle and the end caps of the cylinder. In either event, it will be understood in the descriptions which follow that such systems are operating and their functions will be assumed to take place in the manner described below.

Returning to FIGS. 4A through 4C and FIGS. 5A through 5C, and with concurrent reference thereto, ventricular assist device 50 includes a cylinder 51 defining a cylinder bore 52 therethrough. Cylinder 51 further defines closed ends 58 and 59. Cylinder 51 also supports an input coupler 53 and an output coupler 54 both of which communicate with the interior of cylinder bore 52. A shuttle 55 is generally cylindrical and is precisely fitted within cylinder bore 52 so as to be freely movable therein. Shuttle 55 further defines a face 56 and a face 57. A cylinder head 65 comprises a volume within cylinder bore 52 confined by closed end 58 and face 56 of shuttle 55 together with a portion of cylinder bore 52 therebetween. A second cylinder head 66 comprises a volume within cylinder bore 52 confined by closed end 59 and face 57 of shuttle 55 together with a portion of cylinder bore 52 therebetween. Shuttle 26 also defines a plurality of blood flow channels 60, 61 and 62. Blood flow channel 60 is open at face 57 and closed at face 56. Blood flow channel 61 is closed at face 57 and open at face 56 of shuttle 55. Finally, blood flow channel 62 is open at face 57 and closed at face 56.

Figure 4A:
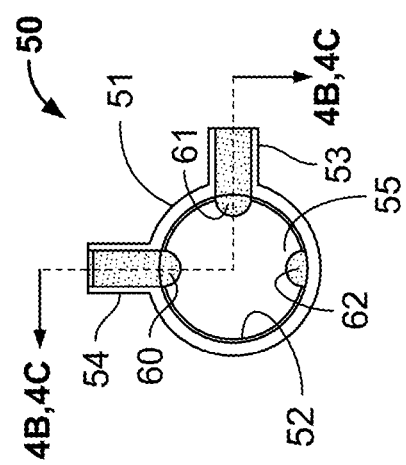

In operation, FIG. 4A sets forth a cross section view of ventricular assist device FIG. 4A sets forth ventricular assist device 50 at the start of a pump cycle which is selected to correspond to a pump stroke initiated as shuttle 55 is at its left position within cylinder 51 and shuttle 55 is rotated to align blood flow channel 61 with input 53 and to align blood flow channel 60 with output 54. As a result, blood flow channel 62 is simultaneously blocked by this rotational position of shuttle 55. The particular point in the operative cycle of ventricular assist device 50 which has been selected as the initial point to initiate an illustrative pump cycle is chosen for convenience. Any point in the operative cycle of ventricular assist device 50 could also serve as a starting point for describing a pump cycle.

FIG. 4B shows shuttle 55 at the initiation of an illustrative pump cycle in which shuttle 55 is at its left position in which face 56 of shuttle 55 is close to end 58 of cylinder 51. At this point, the volume of cylinder head 65 is at a minimum and is near zero. Simultaneously, the left and the position of shuttle 55 distances face 57 of shuttle 55 away from end 59 of cylinder 51. As a result, cylinder head 66 defines a maximum volume.

In accordance with the double acting character of ventricular assist device 50, it will be noted that cylinder head volumes 65 and 66 on each side of shuttle 55 are oppositely changed in volume as shuttle 55 moves within cylinder bore 52. Concurrently, as shuttle 55 moves, one cylinder head is increased in volume while the other cylinder head is decreased in volume. The proper direction of blood flow into and outwardly from the cylinder heads is directed by the alignment of the appropriate blood flow channel with the input and output as shuttle 55 is rotated between each left-to-right and right-to-left linear movement of shuttle 55. This facilitates the double acting operation of ventricular assist device 50 as each stroke of shuttle 55 simultaneously displaces the blood volume in one cylinder head through the output while drawing a quantity of blood into the opposite cylinder head through the input.

The pump stroke begins as shuttle 55 is driven to the right toward end 59 of cylinder 51 in the direction indicated by arrow 63. The movement of shuttle 55 in the direction indicated by arrow 63 increases the volume within cylinder head 65 which, in turn, draws blood from input 53 into channel 61 in the direction indicated by arrow 67. As the shuttle movement in the direction indicated by arrow 63 continues, the volume of cylinder head 65 is further increased drawing additional blood into cylinder head 65 and filling cylinder head 65 with blood until shuttle 55 reaches its extreme right position shown in FIG. 4C. Simultaneously, as shuttle 55 is driven to the right toward end 59 of cylinder 51 in the direction indicated by arrow 63, the movement of shuttle 55 displaces the volume within cylinder head 66 which, in turn, forces blood to flow through channel 60 in the direction indicated by arrow 64. As the shuttle movement in the direction indicated by arrow 63 continues, the volume of cylinder head 66 is further displaced causing continued blood flow in the direction indicated by arrow 64 though output 54.

FIG. 4C shows ventricular assist device 50 at the point at which shuttle 55 has moved fully to the right and face 57 of shuttle 55 is against end 59 of cylinder 51. At this point, a maximum volume of blood is confined within cylinder head 65 and a minimum volume of blood is confined within cylinder head 66. Shuttle 55 is then rotated from the position shown in FIG. 4A to the position shown in FIG. 5A.

FIG. 5A sets forth a section view of ventricular assist device 50 at the midpoint of a pump cycle at which shuttle 55 is rotated in the direction indicated by arrow 70 to align channel 61 with output 54 and to align blood flow channel 62 with input 53. As a result, output 54 is aligned with channel 61 of shuttle 55 while blood flow channel 62 is aligned with input 53. Blood flow channel 60 is simultaneously blocked by this rotational position of shuttle 55.

FIG. 5B shows shuttle 55 at its right position in which face 56 of shuttle 55 is farthest from end 58 of cylinder 51 and face 57 is closest to end 59 of cylinder 51. At this point, the volume of cylinder head 65 is at its maximum while the volume of cylinder head 66 is at its minimum. The pump stroke continues as shuttle 55 is driven to the left toward end 58 of cylinder 51 in the direction indicated by arrow 71. The movement of shuttle 55 in the direction indicated by arrow 71 displaces the volume within cylinder head 65 which, in turn, drives blood into channel 61 and outwardly through output 54 in the direction indicated by arrow 72. This movement of shuttle 55 also increases the volume of cylinder head 66 drawing blood through input 53 into channel 62 in the direction indicated by arrow 73. As the leftward shuttle movement in the direction indicated by arrow 71 continues, the volume of blood within cylinder head 65 is further displaced forcing additional blood from cylinder head 65 while blood continues to be drawn into channel 62 filling cylinder head 66 until shuttle 55 reaches its extreme left position shown in FIG. 5C.

FIG. 5C shows ventricular assist device 50 at the point at which shuttle 55 has moved fully to the left and face 56 of shuttle 55 is against end 58 of cylinder 51. At this point, the confined blood volume blood volume within cylinder head 65 has been displaced outwardly through output 54 and a new volume of blood is confined within cylinder head 66. Shuttle 55 is then rotated from the position shown in FIG. 5A back to the position shown in FIG. 4A at which point the pump cycle is complete and is repeated in the above scribed sequence.

Accordingly, the above-described sequence of operations is carried forward on a repetitive basis as ventricular assist device 50 performs to provide a compact and highly efficient ventricular assist device utilizing a double acting pumping action. This pumping action is carried forward as blood flow channel 61 is rotated into alignment with input 53 and blood flow channel 60 is rotated into alignment with output 54 each time that shuttle 55 is moved to the right (arrow 63) while blood low channel 61 is rotated into alignment with output 54 and blood flow channel 62 is rotated into alignment with input 53 each time that shuttle 55 is moved to the left (arrow 71). Cylinder head 65 is filled with a blood volume and the blood volume within cylinder head 66 is displaced during each movement of shuttle 55 to the right. Conversely, cylinder head 66 is filled with a blood volume and the blood volume within cylinder head 65 is displaced during each movement of shuttle 55 to the left.

Generally, movement of blood into the shuttle may be simultaneous with movement of blood out of the shuttle. This movement of blood may be generated by a pumping cycle, which may be matched to sinus rhythm of the recipient when a ventricular assist device is being employed, and then adjusted if blood pressure needs to be higher or lower, or if another parameter (e.g., oxygen level or dissolved carbon dioxide level) indicates that adjustment is needed. Parameters may be detected, for example, using electrodes attached to the recipient's native heart that receive signals from the recipient's native heart or brain (e.g., via the sinoatrial node), which are then used to modulate the pumping cycle of a ventricular assist device. The modulation may include actuating the ventricular assist device to pump when the native heart is at rest or in diastole, or pump at a particular phase of the cardiac cycle.

Pumping Blood Using an Artificial Heart

When the housing is part of an artificial heart, implanting may include coupling a first port of the plurality of ports to the aorta of the recipient, coupling a second port of the plurality of ports to the pulmonary artery of the recipient, coupling a third port of the plurality of ports to the inferior vena cava and the superior vena cava of the recipient, and coupling a fourth port of the plurality of ports to the pulmonary vein of the recipient.

In general, movement of blood into the shuttle is simultaneous with the movement of blood out of the shuttle. This movement of blood is generated by a pumping cycle, which may be predetermined based on parameters set by a physician, and then adjusted as necessary, if blood pressure needs to be higher or lower. In some embodiments, the speed of the pumping cycle (or other cycle parameters) may be automatically adjusted based on a blood pressure of the recipient. For example, the controller may automatically adjust the speed of the pumping cycle based on feedback from pressure sensors associated with the pumping devices. Alternatively or additionally, the speed of the pumping cycle may be manually adjusted by the recipient or a physician. In addition to the maintenance or modification of blood pressure, the artificial heart may also be responsive to oxygen levels in the blood through use of a blood oximeter or pulse oximeter, or the measurement of dissolved carbon dioxide with a carbon dioxide sensor.

Furthermore, methods for treating heart failure are described herein. The methods generally include implanting a housing into a recipient. The housing may include a shuttle that linearly reciprocates to simultaneously move blood into and out of the housing. Furthermore, the shuttle may be rotated to direct the flow of blood into and out of the housing. The linear reciprocation and rotation of the shuttle typically generates a pumping cycle.

Heart failure may be treated by implanting either a ventricular assist device or an artificial heart. In the same manner as noted above, the speed of the pumping cycle (or other cycle parameters) may be automatically adjusted based on a blood pressure of the recipient. For example, the controller may automatically adjust the speed of the pumping cycle based on feedback from pressure sensors associated with the pumping devices. Alternatively or additionally, the speed of the pumping cycle may be manually adjusted by the recipient or a physician. Types of heart failure that may be treated include heart failure attributed to left-sided heart failure, right-sided heart failure, biventricular heart failure, cardiomyopathy, or an infection.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated.

The invention claimed is:

1. A device for pumping blood comprising:
   a cylindrical housing comprising an exterior, a plurality of ports, a first end, and a second end, the first and second ends defining a chamber therebetween;
   a shuttle within the chamber, the shuttle comprising an outer sleeve defining a hollow interior containing a plurality of magnets, and one or more channels longitudinally extending along the outer sleeve;
   a clearance gap sized to prevent passage of red blood cells between the housing and the shuttle; and
   a magnetic actuation system operable to effect linear and rotational motion to the shuttle,
   wherein the linear motion of the shuttle pumps blood into and out of the chamber according to a pumping cycle, and the rotational motion of the shuttle selectively directs the flow of blood through the plurality of ports.

2. The device of claim 1, wherein the housing, the shuttle, or both, comprise a ceramic material.

3. The device of claim 2, wherein the ceramic material comprises sapphire or synthetic variants thereof.

4. The device of claim 2, wherein the ceramic material comprises zirconia or synthetic variants thereof.

5. The device of claim 1, wherein the device further comprises a manifold.

6. The device of claim 5, wherein the manifold comprises a first inlet and a second inlet, and a first outlet and a second outlet, wherein the first and second inlets are in fluid communication with corresponding inlet ports of the plurality of ports, and the first and second outlets are in fluid communication with corresponding outlet ports of the plurality of ports.

7. The device of claim 5, wherein the manifold comprises a single inlet and a single outlet in fluid communication with corresponding inlet and outlet ports of the plurality of ports.

8. The device of claim 1, wherein the clearance gap ranges from about 2.0 to 4.0 µm.

9. The device of claim 1, wherein the magnetic actuation system comprises a plurality of linear motor coils encircling the cylindrical housing, and a plurality of rotational coils disposed at each of the first and second ends of the cylindrical housing.

10. The device of claim 1, wherein the magnetic actuation system comprises a plurality of linear motor coils encircling the cylindrical housing and a permanent magnet disposed within each of the first and second ends of the cylindrical housing.

11. The device of claim 1, wherein the device comprises a controller operably coupled to the magnetic actuation system and configured to control the pumping cycle.

12. The device of claim 11, wherein the controller is operably connected to a pressure sensor.

13. The device of claim 11, wherein the controller is configured to wirelessly transmit information from the device to an external device.

14. The device of claim 1, further comprising a coating on the housing exterior.

15. The device of claim 1, wherein the device is an artificial heart.

16. A device for pumping blood comprising:
- a cylindrical housing comprising an exterior, a plurality of ports, a first end, and a second end, the first and second ends defining a chamber therebetween;
- a shuttle within the chamber, the shuttle comprising an outer sleeve defining a hollow interior containing a plurality of magnets, and one or more channels longitudinally extending along the outer sleeve; and
- a magnetic actuation system operable to effect linear and rotational motion to the shuttle, the magnetic actuation system comprising a plurality of linear motor coils encircling the cylindrical housing, and a plurality of rotational coils disposed at each of the first and second ends of the cylindrical housing,
- wherein the linear motion of the shuttle pumps blood into and out of the chamber according to a pumping cycle, and the rotational motion of the shuttle selectively directs the flow of blood through the plurality of ports.

17. The device of claim 16, wherein the housing, the shuttle, or both, comprise a ceramic material.

18. The device of claim 17, wherein the ceramic material comprises sapphire or synthetic variants thereof.

19. The device of claim 17, wherein the ceramic material comprises zirconia or synthetic variants thereof.

20. The device of claim 16, wherein the device further comprises a manifold.

21. The device of claim 20, wherein the manifold comprises a first inlet and a second inlet, and a first outlet and a second outlet, wherein the first and second inlets are in fluid communication with corresponding inlet ports of the plurality of ports, and the first and second outlets are in fluid communication with corresponding outlet ports of the plurality of ports.

22. The device of claim 20, wherein the manifold comprises a single inlet and a single outlet in fluid communication with corresponding inlet and outlet ports of the plurality of ports.

23. The device of claim 16, wherein the magnetic actuation system comprises a plurality of linear motor coils encircling the cylindrical housing and a permanent magnet disposed within each of the first and second ends of the cylindrical housing.

24. The device of claim 16, wherein the device comprises a controller operably coupled to the magnetic actuation system and configured to control the pumping cycle.

25. The device of claim 24, wherein the controller is operably connected to a pressure sensor.

26. The device of claim 24, wherein the controller is configured to wirelessly transmit information from the device to an external device.

27. The device of claim 16, further comprising a coating on the housing exterior.

28. The device of claim 16, wherein the device is an artificial heart.

* * * * *